United States Patent
Fürstner et al.

(10) Patent No.: US 9,556,209 B2
(45) Date of Patent: Jan. 31, 2017

(54) **PROCESS FOR THE RUTHENIUM CATALYZED *TRANS*-SELECTIVE HYDROSTANNATION OF ALKYNES**

(71) Applicant: STUDIENGESELLSCHAFT KOHLE MBH, Mülheim (DE)

(72) Inventors: Alois Fürstner, Mülheim (DE); Stephan Rummelt, Lörrach (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 15/030,897

(22) PCT Filed: Oct. 14, 2014

(86) PCT No.: PCT/EP2014/072068
§ 371 (c)(1),
(2) Date: Apr. 21, 2016

(87) PCT Pub. No.: WO2015/059006
PCT Pub. Date: Apr. 30, 2015

(65) Prior Publication Data
US 2016/0251382 A1    Sep. 1, 2016

(30) Foreign Application Priority Data
Oct. 22, 2013 (EP) .................................. 13189792

(51) Int. Cl.
C07F 7/22 (2006.01)
B01J 31/22 (2006.01)
C07F 15/00 (2006.01)

(52) U.S. Cl.
CPC .......... *C07F 7/2212* (2013.01); *B01J 31/2295* (2013.01); *C07F 15/0046* (2013.01); *B01J 2231/323* (2013.01); *B01J 2531/821* (2013.01)

(58) Field of Classification Search
CPC C07F 7/2212; B01J 31/2295; B01J 2231/323; B01J 2531/821
USPC ......................................................... 548/440
See application file for complete search history.

(56) References Cited

PUBLICATIONS

K. Kikukawa et al., "Regioselective Hydrostannation of Terminal Acetylenes Under Transtition Metal Catalysis", Chem. Lett. 1988, 881-884.

*Primary Examiner* — Kristin Vajda
(74) *Attorney, Agent, or Firm* — Norris McLaughlin & Marcus, P.A.

(57) ABSTRACT

The present invention refers to a process for the ruthenium-catalyzed trans-selective hydrostannation of alkynes and the so-obtained products. The inventive process makes use of a tin hydride which is reacted with an alkyne in the presence of a cyclopentadienyl-coordinated ruthenium catalyst.

10 Claims, No Drawings

PROCESS FOR THE RUTHENIUM CATALYZED *TRANS*-SELECTIVE HYDROSTANNATION OF ALKYNES

This application is a 371 of PCT/EP2014/072068, filed Oct. 14, 2014, which claims foreign priority benefit under 35 U.S.C. §119 of the European Patent Application No. 13189792.8 filed Oct. 22, 2013, the disclosures of which are incorporated herein by reference.

The present invention refers to a process for the ruthenium catalyzed trans-selective hydrostannation of alkynes and the so-obtained products.

The hydrostannation of alkynes is an indispensable method for the synthesis of alkenyltin reagents (alkenylstannanes) that find extensive use in preparative chemistry (M. Pereyre, J. P. Quintard, A. Rahm, *Tin in Organic Synthesis*, Butterworth, London, 1987; A. Orita, J. Otera, in: *Main Group Metals in Organic Synthesis* (H. Yamamoto, K. Oshima, Eds.), Wiley-VCH, Weinheim, 2004, Vol. 2, p. 621). The Stille cross coupling reaction is arguably the most important application of organotin reagents in general and alkenyltin reagents in particular (V. Farina, V. Krishnamurthy, W. J. Scott, *Org. React.* 1997, 50, 1). Other important applications of alkenyltin reagents involve, but are not limited to, metal-for-tin exchange, in particular lithium-for-tin exchange, as well as halogen-for-tin exchange reactions.

Tin hydrides can be added to alkynes under conditions involving the formation of free radicals as the reactive intermediates. To this end, the addition reactions are usually carried out at elevated temperatures in the presence of radical initiators such as azoisobutyronitrile (AIBN) or under ultrasonication. Under such conditions, alkynes usually afford E/Z-mixtures of the corresponding alkenylstannanes (J. A. Marshall in: *Organometallics in Synthesis* (M. Schlosser, Ed.), Wiley, Chichester, 2002, $2^{nd}$ Ed., p. 353). The product ratio can change with time as the tin radicals involved in the reactions can lead to secondary isomerization of the kinetic products initially formed. Radical hydrostannation reactions are usually not applicable to substrates that contain other sites of unsaturation (alkenes, allenes) in addition to the alkyne, or that contain other functional groups that will react with intermediate tin radicals (halides, azides, thioethers, thiocarbamates etc).

Alternatively, tin hydrides can be added to alkynes in the presence of metal catalysts (N. D. Smith, J. Mancuso, M. Lautens, *Chem. Rev.* 2000, 100, 3257). A large variety of different transition metal catalysts has been investigated, with palladium, nickel, rhodium and molybdenum being most commonly used. Largely independent of the chosen transition metal catalyst and as a consequence of the proposed reaction mechanism, such additions usually occur by suprafacial delivery of hydrogen and tin to the same π-face of a given starting material (cis-addition mode), thus furnishing the E-isomer of the resulting alkenylstannane. Although the exact mechanisms of such reactions are not always clear, catalytic cycles based on oxidative addition of the catalyst into the Sn—H bond, hydrometalation of the alkyne substrate, followed by reductive elimination are generally proposed.

Exceptions of this cis-addition mode in transition metal catalyzed hydrostannation reactions are rare and usually substrate dependent. Thus, certain acetylenes conjugated to strongly electron withdrawing ketone group were shown to give products derived from formal trans-addition under palladium catalysis, whereas the corresponding acetylenic esters react by the normal cis-addition mode under the same reaction conditions (J. C. Cochran et al., *Tetrahedron Lett.* 1990, 31, 6621). It can therefore not be excluded that a secondary isomerization process might account for the unusual stereochemical outcome in the ketone series. Likewise, terminal alkynes were found to produce product mixtures containing varying amounts of formal trans-addition products in the presence of various transition metal catalysts (K. Kikukawa et al., *Chem. Lett.* 1988, 881).

Highly selective formal trans-hydrostannations of terminal or internal alkynes have so far only been accomplished with the help of strong Lewis acid additives or catalysts (N. Asao et al., *J. Org. Chem.* 1996, 61, 4568; V. Gevorgyan et al., *Chem. Commun.* 1998, 37; M. S. Oderinde et al., *Angew. Chem.* 2012, 124, 9972). The best additives or catalysts currently known are $ZrCl_4$, $HfCl_4$ and $B(C_6F_5)_3$, which are thought to abstract the hydride from the $Bu_3SnH$ reagent with formation of a transient $Bu_3Sn^+$ species that coordinates the alkyne. Hydride delivery to the resulting complex occurs trans to the bulky $R_3Sn$-residue and hence results in formal trans-hydrostannation. Although the trans-selectivity is usually excellent, the very high Lewis acidity of the additives or catalysts severely limits the compatibility of this method with functional groups; even a simple benzyl ether was reported to quench the activity of $ZrCl_4$ and hence prevent the trans-hydrostannation from occurring (N. Asao et al., *J. Org. Chem.* 1996, 61, 4568). The very high Lewis acidity of the additives or catalysts is also the reason why the reaction is best carried out in unfunctionalized hydrocarbon solvents such as toluene or hexane, in which $ZrCl_4$ as the preferred catalyst is not well soluble. The use of THF or $CH_2Cl_2$, which dissolve $ZrCl_4$ and certain substrates more effectively, were reported to giver lower stereoselectivities and chemical yields. Another disadvantage is the fact that the trans-hydrostannation of internal alkynes requires stoichiometric amounts of $ZrCl_4$ for optimal results.

The inventors of the present invention found the first broadly applicable, functional group tolerant and highly stereoselective ruthenium catalyzed trans-hydrostannation of alkynes. Previous ruthenium catalyzed hydrostannations of terminal alkynes were shown to deliver product mixtures containing different regio- as well as stereoisomers that are of little preparative use (K. Kikukawa et al., *Chem. Lett.* 1988, 881). In contrast, the present invention is directed to a process for highly stereoselective trans-hydrostannation of alkynes comprising the steps of reacting an alkyne of the formula I

with a tin hydride of the formula $X^1X^2X^3SnH$ in the presence of a ruthenium catalyst to yield an alkene of the general formula (II):

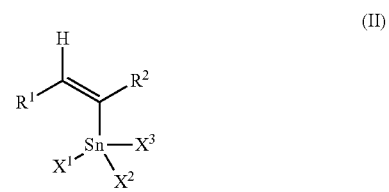

In the alkyne of the general formula (I) and in the alkene of the general formula (II), respectively, $R^1$ and $R^2$ may be the same or different and may each be selected from:

I. straight chain or branched chain aliphatic hydrocarbons, preferably having 1 to 20 carbon atoms, or cyclic aliphatic hydrocarbons, preferably having 3 to 20 carbon atoms, said aliphatic hydrocarbons optionally including heteroatoms and/or aromatic hydrocarbons and/or heteroaromatic hydrocarbons in the chain and/or having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, or heteroatoms, or II. aromatic hydrocarbons having 5 to 20 carbon atoms or heteroaromatic hydrocarbons having 1 to 20 carbon atoms, said aromatic or heteroaromatic hydrocarbons each optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, heteroatoms, or one of $R^1$ and $R^2$ is selected from hydrogen, halogen, —SiR*RR*, wherein R*, R, R* can be the same or different and may have the meaning as given under I. and II., and the other of $R^1$ and $R^2$ has the meaning as given under I. or II.

or $R^1$ and $R^2$ together form an aliphatic hydrocarbon chain having 6 to 30 carbon atoms, optionally including heteroatoms and/or aromatic hydrocarbons in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, said aliphatic hydrocarbon chain optionally being substituted by one or more substituents selected from heterosubstituents, straight chain, branched chain, cyclic aliphatic $C_1$ to $C_{20}$ hydrocarbons, $C_6$ to $C_{20}$ aromatic hydrocarbon, $C_5$ to $C_{20}$ heteroaromatic hydrocarbon, aryl-($C_1$-$C_6$)-alkyl, or heteroaryl-($C_1$-$C_6$)-alkyl or heteroatoms.

Preferably, $R^1$ and $R^2$ may be the same or different and may each be selected from straight chain or branched chain aliphatic hydrocarbons having 1 to 20 carbon atoms optionally including heteroatoms and/or aromatic hydrocarbons in the chain or aromatic hydrocarbons having 5 to 20 carbon atoms, optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, or heteroatoms, or $R^1$ and $R^2$ together form an aliphatic hydrocarbon chain structure having 8 to 20 carbon atoms, optionally including heteroatoms and/or aromatic hydrocarbons in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, said chain structure optionally being substituted by one or more substituents selected from heterosubstituents, straight chain, branched chain, cyclic aliphatic $C_1$ to $C_{20}$ hydrocarbons, $C_6$ to $C_{20}$ aromatic hydrocarbon, $C_5$ to $C_{20}$ heteroaromatic hydrocarbon, aryl-($C_1$-$C_6$)-alkyl, or heteroaryl-($C_1$-$C_6$)-alkyl, or one of $R^1$ and $R^2$ is selected from hydrogen, halogen, —SiR*RR*, wherein R*, R, R* can be the same or different and may each be selected from straight chain or branched chain aliphatic hydrocarbons having 1 to 20 carbon atoms optionally including heteroatoms and/or aromatic hydrocarbons in the chain or aromatic hydrocarbons having 5 to 20 carbon atoms, optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, or heteroatoms.

$R^1$ and $R^2$ should preferably have a lower affinity to the Ru-central atom in the ruthenium complex than the alkyne moiety in order to avoid blocking of the reactive site thereof.

The substituents $X^1$, $X^2$ and $X^3$ in the tin hydride of the formula $X^1X^2X^3SnH$ may be the same or different and may each be selected from hydrogen, straight chain, branched chain or cyclic aliphatic hydrocarbons, preferably having 1 to 20, preferably 1 to 16 carbon atoms, or aromatic hydrocarbons preferably having 6 to 22, preferably 6 to 14 carbon atoms, or two of $X^1$ $X^2$ and $X^3$ together form an aliphatic hydrocarbon chain having 2 to 20 carbon atoms, preferably 2 to 10 carbon atoms in the chain, including said aliphatic hydrocarbons being bound to Sn via oxygen (such as alkoxy), said aliphatic hydrocarbon group optionally including heteroatoms in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_1$ to $C_{20}$ heteroaromatic hydrocarbon or aryl-($C_1$-$C_6$)-alkyl, heteroaryl-($C_1$-$C_6$)-alkyl, having identical or different alkyl groups with 2 to 12 carbon atoms, halogen or heteroatoms wherein at least two of $X^1$, $X^2$ and $X^3$ are not hydrogen In said formula, $X^1X^2X^3SnH$, any hydrogen directly bond to the Sn atom may also be deuterium.

Preferably, the tin hydride of the formula $X^1X^2X^3SnH$ is represented by the formula in which $X^1$, $X^2$ and $X^3$ may be the same or different and may each be selected from straight chain, branched chain or cyclic $C_1$ to $C_{10}$ aliphatic hydrocarbons each optionally being substituted by methyl, ethyl, propyl, butyl or isomers thereof, or one or more fluorine atoms. Examples of preferred tin hydrides are (lower alkyl)$_3$SnH or (lower alkyl)$_2$SnH$_2$ including partially or fully halogenated lower alkyl, such as Me$_3$SnH, Bu$_3$SnH, Bu$_2$SnH$_2$, Cy$_3$SnH (Cy=cyclohexyl), (octyl)$_3$SnH, [CF$_3$(CF$_2$)$_5$(CH$_2$)$_2$]$_3$SnH, [CF$_3$(CF$_2$)$_3$(CH$_2$)$_2$]$_3$SnH.

In another embodiment of the current invention, the higher isotopomers of the tin hydride reagents of the general formula $X^1X^2X^3SnH$ are used, in particular the corresponding tin deuterides of the general formula $X^1X^2X^3SnD$, wherein the substituents $X^1$, $X^2$ and $X^3$ can be chosen as defined above.

The catalyst used in the inventive process is a cyclopentadienyl-coordinated ruthenium complex containing the following substructure:

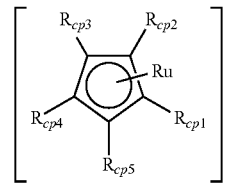

wherein $R_{cp1}$ to $R_{cp5}$ may be the same or different and may each be selected from hydrogen or from straight chain, branched chain or cyclic aliphatic hydrocarbons, preferably having 1 to 20 carbon atoms, optionally including heteroatoms and/or aromatic hydrocarbons in the chain and/or optionally having one or more substituents selected from $C_1$-$C_{20}$-alkyl, heterocycloalkyl, $C_6$ to $C_{20}$ aromatic hydrocarbon, $C_5$ to $C_{20}$ heteroaromatic hydrocarbon or aryl-($C_1$-

$C_6$)-alkyl, heteroaryl-($C_1$-$C_6$)-alkyl or heteroatoms and wherein further ligands are coordinated to the central atom ruthenium.

Preferred are catalysts [Cp*RuL$_3$]X wherein Cp*=$\eta^5$-$C_5R_{5cp}$ with each $R_{cp}$ being H or preferably $CH_3$, and L being the same or different ligand/substituent and being selected from two electron-donating ligands/substituents such as $CH_3CN$, cycloalkadiene having 8 to 12 carbon atoms, or a catalyst complex of the formula [Cp*RuY$_n$] wherein Cp*=$\eta^5$-$C_6R_{5cp}$ with each $R_{cp}$ being H or preferably $CH_3$, and Y is an anionic ligand and being selected from hydrogen, halogen and n=2, 3, or a dimer or oligomer of the formula [Cp*RuY$_2$]$_n$ wherein Cp*=$\eta^5$-$C_5R_5$ with R being H or $CH_3$ and Y is an anionic ligand and being selected from hydrogen, halogen and n≥2. A preferred Ru-complex can be a cationic complex with an anionic counter ion X that is weakly coordinating, such as $PF_6^-$, $SbF_6^-$, $BF_4^-$, $ClO_4^-$, $F_3CCOO^-$, $Tf_2N^-$, (Tf=trifluoromethanesulfonyl), $TfO^-$, tosyl, $[B[3,5-(CF_3)_2C_6H_3]_4]^-$, $B(C_6F_5)_4^-$), $Al(OC(CF_3)_3)_4^-$ The solvent used in the inventive process should be a low donor solvent and may be selected from aliphatic, cycloaliphatic solvents, fluorinated hydrocarbons, esters, ethers, ketones or mixtures thereof which may be substituted by one or more heteroatoms such as pentane, hexane, $CHCl_3$, $CH_2Cl_2$, 1,2-dichloroethane, $CH_3CN$, ethyl acetate, acetone, THF, diethyl ether or methyl tert-butyl ether, 1,2-dimethoxyethane (glyme), bis(2-methoxyethyl)ether (diglyme), benzotrifluoride, as long as they are not detrimental to the catalysed reaction. If the alkyne of the formula (I) itself is a liquid or in a liquid state, there might be no need for a separate solvent. The catalyst is generally used in a molar ratio of 0.1 to 10 mol-%, preferably 1 to 5 mol-% referred to the alkyne of the general formula (I).

The inventive process can be carried out in a temperature range from −78° C. to 100° C., preferably at ambient temperature of between 0° and 30° C., and it proceeds at normal pressure already. If needed, the reaction can be carried out in a protective atmosphere such as nitrogen or argon.

A heterosubstituent as defined according to the invention can be selected from —O—, =O, F, Cl, Br, I, CN, $NO_2$, a monohalogenomethyl group, a dihalogenomethyl group, a trihalogenomethyl group, $CF(CF_3)_2$, $SF_5$, amine bound through N atom, —O-alkyl (alkoxy), —O-aryl, —O—SiR$^S_3$, S—R$^S$, S(O)—R$^S$, S(O)$_2$—R$^S$, CO$_2$—R$^S$, amide, bound through C or N atom, formyl group, C(O)—R$^S$. R$^S_3$ may be, independently from each other, the same or different and may be each an aliphatic, heteroaliphatic, aromatic or heteroaromatic group, each optionally being further substituted by one or more heterosubstituents, aliphatic, heteroaliphatic, aromatic or heteroaromatic groups. Preferably, the heterosubstituent is selected from =O, F, Cl, Br, I, CN, $NO_2$, a monohalogenomethyl group, a dihalogenomethyl group, a trihalogenomethyl group, $CF(CF_3)_2$, $SF_5$, amine bound through N atom, —O-alkyl (alkoxy), —O-aryl.

In more detail, $C_1$-$C_{20}$-alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be lower alkyl such as $C_1$-$C_5$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might preferably be $C_3$-$C_{10}$-alkyl and may be cyclopropyl, cyclobutyl, cyclopentyl, cyclohexyl or cycloheptyl.

Alkenyl might be $C_2$-$C_{20}$ alkenyl. Alkynyl might be $C_2$-$C_{20}$ alkynyl.

Halogen is F, Cl, Br or I.

Alkoxy is preferably $C_2$-$C_{10}$ alkoxy such as methoxy, ethoxy, propoxy, iso-propoxy, tert-butoxy etc.

Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Including heteroatoms and/or aromatic hydrocarbons in the chain means that one or more carbon atoms in the chain might be replaced by heteroatoms such as N, O or S or part of an aromatic ring structure.

Aryl might be phenyl, naphthyl, biphenyl, anthracenyl, and other polycondensed aromatic systems.

Aryl-($C_1$-$C_6$)-alkyl might be benzyl or substituted benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2, 1,3-benzoxadiazol-5-yl.

The invention is further illustrated as follows:

The inventors have carried out an initial screening of catalysts and solvents using tributyltin hydride as the reagent for the trans-hydrostannation of alkynes. The results are indicated in the following Table 1.

TABLE 1

Initial screening for the trans-hydrostannation using cycloalkyne 1 as the substrate; for the sake of comparison, all reactions were stopped after only 15 min reaction time

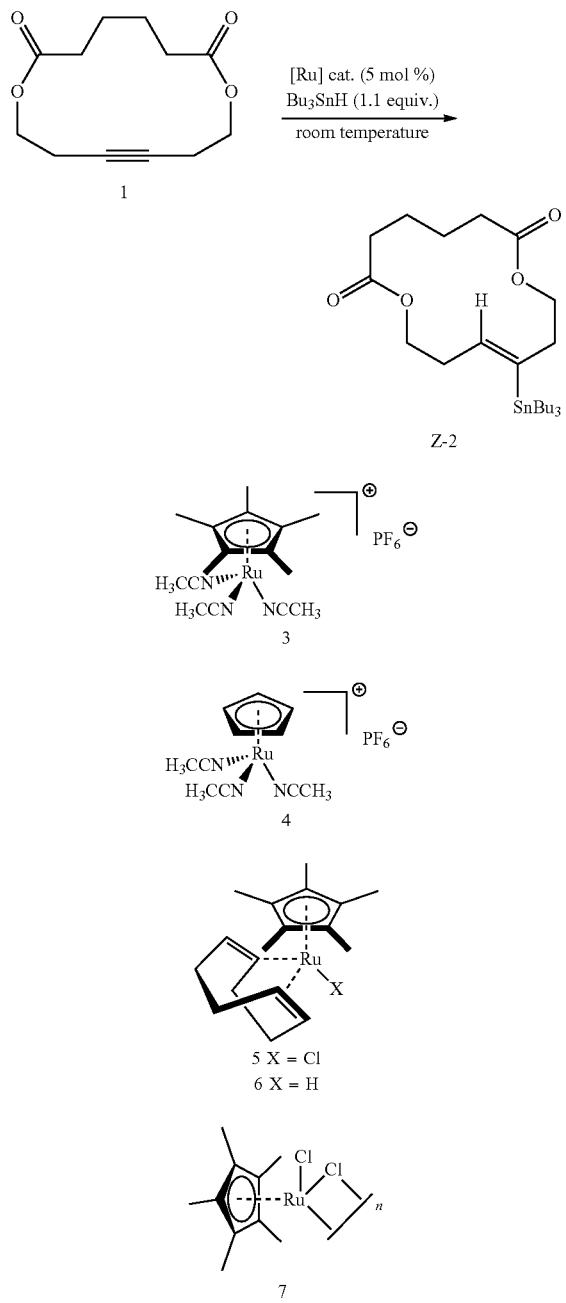

| Entry | Solvent | [Ru] | Z:E | Yield (%) |
|---|---|---|---|---|
| 1 | CH$_2$Cl$_2$ | 3 | 86:14 | 96 |
| 2 | dichloroethane | 3 | 82:18 | 97 |
| 3 | acetone | 3 | 83:17 | 41 [a] |
| 4 | MeCN | 3 | 82:18 | 66 |
| 5 | Et$_2$O/CH$_2$Cl$_2$ (7:3) | 3 | 85:15 | quant. [a] |
| 6 | diglyme | 3 | 83:17 | 81 |
| 7 | CH$_2$Cl$_2$ | 4 | 63:37 | 83 |
| 8 | CH$_2$Cl$_2$ | 5 | 84:16 | 34 |
| 9 | CH$_2$Cl$_2$ | 7 | 89:11 | 85 |
| 10 | CH$_2$Cl$_2$ | 3 | 85:15 | 94 [b] |
| 11 | CH$_2$Cl$_2$ | 3 | 86:14 | 78 [c] |

[a] conversion rather than isolated yield;
[b] the reaction was performed in the dark;
[c] the reaction was performed in the presence of 1 equivalent of TEMPO (2,2,6,6-tetramethyl-piperidin-1-oxyl; free radical)

The reactions shown in Table 1 were carried out at 0.1 M concentration in CH$_2$Cl$_2$ under argon; however, very similar results in terms of yield and selectivity were obtained at different concentrations. The E:Z ratios were determined by NMR and refer to the crude material prior to work up. Unless stated otherwise, the yields refer to analytically pure isolated material.

The inventors found that trans-selective hydrostannations proceed very rapidly in the presence of [Cp*Ru(MeCN)$_3$]PF$_6$ (3) as one of the preferred catalysts Thus, addition of 5 mol % of this complex to a solution of 1 and Bu$_3$SnH in CH$_2$Cl$_2$ resulted in a very fast (<15 min), clean and highly trans-selective hydrostannation (Z:E≥86:14, NMR) (entry 1). The product was isolated in 96% yield The same excellent stereoselectivity was recorded when the hydrostannation was performed in the dark, which excludes that the major product Z-2 is formed by a secondary photochemical E→Z isomerization (entry 10). Likewise, the reaction proceeds with the same selectivity and in good yield when performed in the presence of 1 equivalent of TEMPO, which is known to serve as an efficient radical trap (entry 11). This result demonstrates that the observed trans-addition is not the result of a radical but of a true metal-catalyzed process. Collectively, these data suggest that the observed trans-addition is an inherent feature of the new methodology, and that the reaction is a true hydrostannation rather than an isomerization process.

A brief survey showed that the use of [Cp*Ru(MeCN)$_3$]PF$_6$ (3) in CH$_2$Cl$_2$ is a preferred catalyst. As evident from Table 1, several other solvents or solvent mixtures gave similarly good stereoselectivities and good to excellent yields. However, the use of toluene gave only low conversion. This result is thought to reflect the affinity of [LRu(MeCN)$_3$]$^+$ (L=Cp, Cp*) towards arenes (and other conjugated π-systems), which leads to the formation of kinetically fairly stable adducts of type [Cp*Ru(η$^6$-arene)]$^+$. Other strong donor solvents also tend to give low yields.

Formal replacement of the labile MeCN ligands on the cationic [Cp*Ru]$^+$ template by a kinetically more tightly bound cyclooctadiene (cod) moiety allows the reaction still to proceed but makes it less productive. Thus, the neutral variant [Cp*Ru(cod)Cl] (5) furnished no more than 34% conversion (GC) (entry 8). In this case, the tin reagent itself may help release a cationic species in solution by slow abstraction of the chloride from the ruthenium precatalyst. A similar process might account for the activation of the chloride-bridged complex 7 (entry 9). Although the tested precatalysts greatly differ in efficiency, the E/Z-ratio was similarly high in all cases, which may indicate the formation of a (largely) common active species.

Of mechanistic significance is the observation of the inventors that the exquisite selectivity for trans-hydrostannation is somewhat compromised upon formal replacement of the Cp* unit by the parent unsubstituted cyclopentadienyl (Cp) ring present in [CpRu(MeCN)$_3$]PF$_6$ (4), although the trans-addition product is still formed as the major compound (entry 7 versus entry 1). Since this structural change hardly affects the electronic properties of the ruthenium center, the stereodetermining step of the catalytic cycle likely has a large steric component. A possible rationale is outlined below.

The optimal reaction conditions were applied to a set of representative alkyne derivatives to explore the scope and limitations of the new procedure. As can be seen from the results compiled in Table 2, good to outstanding selectivity for trans-hydrostannation was observed for a variety of substrates and the chemical yields were also good to excellent. In close analogy to other hydrostannation reactions (N. D. Smith, J. Mancuso, M. Lautens, Chem. Rev. 2000, 100, 3257), unsymmetrical alkynes lead to the formation of regioisomers; careful NMR analysis confirmed that either regioisomer derives from a trans-hydrostannation pathway. Ways to largely avoid such mixtures of regioisomers are outlined below for alkyne substrates containing protic functionality.

As pointed out above, the current procedure is also applicable to terminal alkynes as well as to alkynes bearing a heteroelement directly bound to the triple bond; the heteroelements that can be directly bound to the triple bond include silicon and halogen, which are of particular preparative relevance; in these cases, the resulting alkenyltin derivatives are usually formed with excellent regioselectivities. Likewise, it is important to recognize that the hydrostannation of methyl 5-hexynoate as a prototype terminal alkyne substrate led to the alkenylstannane as the largely major isomer, in which the tin residue is bound to the non-terminal carbon atom (Table 2, entry 21). In contrast, hydrostannation of methyl 5-hexynoate under free radical conditions has previously been reported to afford the regioisomeric alkenyltin compound (as a mixture of stereoisomers), in which the tin residue is at the terminal position (J. D. White et al., J. Am. Chem. Soc. 1995, 117, 6224). This different outcome provides further evidence that the current invention is not a radical but a ruthenium-catalyzed process.

A variety of functional groups in the reaction system is tolerated, including ethers, esters, silyl ethers, sulfonates, ketones, phthalimides, azides, amides, Weinreb amides, carbamates, sulfonamides, alkenes, halides, a free carboxylic acid, unprotected hydroxyl groups as well as different heterocycles. This functional group tolerance further corroborates that the observed trans-hydrostannation is not the result of a radical process, since azides or halides are incompatible with tin radicals. Moreover, most of these functional group are not tolerated in the literature-known trans-hydrostannation reactions effected by catalytic or stoichiometric amounts of strong Lewis acids such as $ZrCl_4$, $HfCl_4$ and $B(C_6F_5)_3$ (N. Asao et al., J. Org. Chem. 1996, 61, 4568; V. Gevorgyan et al., Chem. Commun. 1998, 37; M. S. Oderinde et al., Angew. Chem. 2012, 124, 9972).

Further results of the inventors show that the formation of regioisomers in the trans-hydrostannation of unsymmetrical alkynes can be tuned by the choice of the catalyst. A striking illustration is provided in following Scheme 1. Whereas the use of $[Cp*Ru(MeCN)_3]PF_6$ (3) gave a 2.8:1 mixture, the isomer ratio was largely improved in favor of the α-isomer by the use of the oligomeric precursor $[Cp*RuCl_2]_n$ (7) (n≥2) (prepared according to: N. Oshima et al., Chem. Lett. 1984, 1161). This effect is preparatively highly useful and broadly applicable (see below).

Scheme 1.

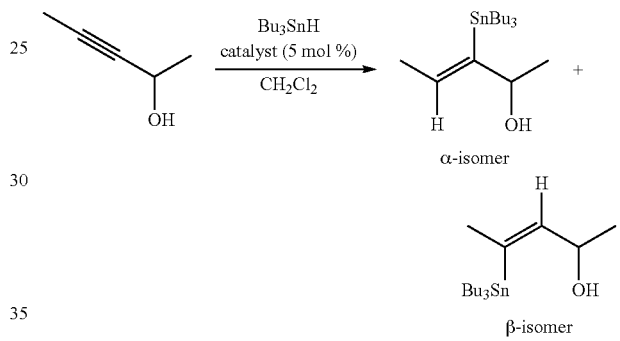

| Catalyst | Combined yield | α:β (NMR) |
|---|---|---|
| $[Cp*Ru(MeCN)_3]PF_6$ (3) | 91% | 2.8:1 |
| $[Cp*RuCl_2]_n$ (7) | 88% | 98:2 |

TABLE 2

Representative examples of alkenylstannanes prepared by the ruthenium-catalyzed trans-hydrostannation reaction; in case where mixtures of regioisomers are obtained, only the major regioisomer is depicted and the reported Z:E ratio refers to this major regioisomer. Unless stated otherwise, all reactions were performed with $Bu_3SnH$ in $CH_2Cl_2$ at ambient temperature using 5 mol % of $[Cp*Ru(MeCN)_3]PF_6$ as the catalyst.

| Entry | Major Product | Overall Yield [a] | regioisomer ratio | Z:E |
|---|---|---|---|---|
| 1 | (structure with SnBu₃) | 94% | — | >99:1 |
| 2 | (structure with AcO, OAc, SnBu₃) | 80% | — | 99:1 |

TABLE 2-continued

Representative examples of alkenylstannanes prepared by the ruthenium-catalyzed trans-hydrostannation reaction; in case where mixtures of regioisomers are obtained, only the major regioisomer is depicted and the reported Z:E ratio refers to this major regioisomer. Unless stated otherwise, all reactions were performed with $Bu_3SnH$ in $CH_2Cl_2$ at ambient temperature using 5 mol % of $[Cp^*Ru(MeCN)_3]PF_6$ as the catalyst.

| Entry | Major Product | Overall Yield [a] | regioisomer ratio | Z:E |
|---|---|---|---|---|
| 3 | (structure with OTs, SnBu₃) | 98% | — | 99:1 |
| 4 | (structure with EtO₂C, CO₂Et, SnBu₃) | 69% | — | >99:1 |
| 5 | (structure with Br, SnBu₃, Br) | 80% | — | 97:3 |
| 6 | (structure with N₃, SnBu₃, N₃) | 56% | — | 98:2 |
| 7 | (diketone structure with SnBu₃) | 94% | — | 99:1 |
| 8 | (bis-Weinreb amide structure with SnBu₃) | 88% | — | 99:1 |
| 9 | (bis-phthalimide structure with SnBu₃) | 98% | — | >99:1 |
| 10 | (stilbene with Bu₃Sn, two CF₃ groups) | quant. | — | n.d. |

TABLE 2-continued

Representative examples of alkenylstannanes prepared by the ruthenium-catalyzed trans-hydrostannation reaction; in case where mixtures of regioisomers are obtained, only the major regioisomer is depicted and the reported Z:E ratio refers to this major regioisomer. Unless stated otherwise, all reactions were performed with $Bu_3SnH$ in $CH_2Cl_2$ at ambient temperature using 5 mol % of $[Cp*Ru(MeCN)_3]PF_6$ as the catalyst.

| Entry | Major Product | Overall Yield [a] | regioisomer ratio | Z:E |
|---|---|---|---|---|
| 11 | (structure with $Bu_3Sn$, phthalate diester) | 97% | — | 95:5 |
| 12 | (structure with HO, $SnBu_3$, $SiMe_3$) | 82% | 96:4 | >99:1 |
| 13 | (structure with MeO-aryl ester, $SnBu_3$, $SiMe_3$) | 98% | 96:4 | >99:1 |
| 14 | (structure with $Et_3Si$, $SnBu_3$, Cl) | 94% | 99:1 | >99:1 |
| 15 | (structure with $SnBu_3$, isopropyl) | 90% | 3.7:1 | 97:3 |
| 16 | (structure with $F_3C$-aryl, $SnBu_3$) | 90% | 1.9:1 | >99:1 |
| 17 | (structure with $SnBu_3$, OH) | 91% | 2.8:1 | >99:1 |
| 18 | (structure with EtO ester, $SnBu_3$) | 90% | 1.5:1 | 99:1 |
| 19 | (structure with HO acid, $SnBu_3$, propyl) | 77% | 1:1 | 99:1 (α) 91-9 (β) |

TABLE 2-continued

Representative examples of alkenylstannanes prepared by the ruthenium-catalyzed trans-hydrostannation reaction; in case where mixtures of regioisomers are obtained, only the major regioisomer is depicted and the reported Z:E ratio refers to this major regioisomer. Unless stated otherwise, all reactions were performed with Bu₃SnH in CH₂Cl₂ at ambient temperature using 5 mol % of [Cp*Ru(MeCN)₃]PF₆ as the catalyst.

| Entry | Major Product | Overall Yield [a] | regioisomer ratio | Z:E |
|---|---|---|---|---|
| 20 | 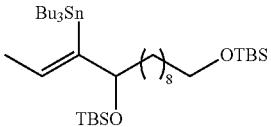 | 82% [b] | 3.6:1 | >99:1 |
| 21 | 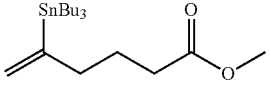 | 73% [c] | 97:3 | |

[a] isolated yield of the product mixture, unless stated otherwise;
[b] conversion (NMR) rather than isolated yield;
[c] a CH₂Cl₂ solution containing both, the alkyne substrate and Bu₃SnH, was slowly added to a solution of the catalyst in CH₂Cl₂;
n.d. = not determined The known affinity of [Cp*Ru] to arenes explains why tolane hardly reacts under the above conditions, but modifying the reactions conditions including testing different Ru-catalysts and tin hydrides should enable the skilled man to find out suitable conditions. The inventors assume that electron withdrawing substituents on the aromatic ring might destabilize sandwich complexes of the general type [Cp*Ru(η⁶-arene)]⁺ (Gill, T. P. et al., *Organometallics* 1, 485-488 (1982); Schmid, A. et al., *Eur. J. Inorg. Chem.* 2255-2263 (2003)). In fact, arylalkynes bearing electron withdrawing groups on the aromatic ring reacted well, although they took longer to reach full conversion (see Table 2, entries 10, 16).

Scheme 2. Possible mechanism

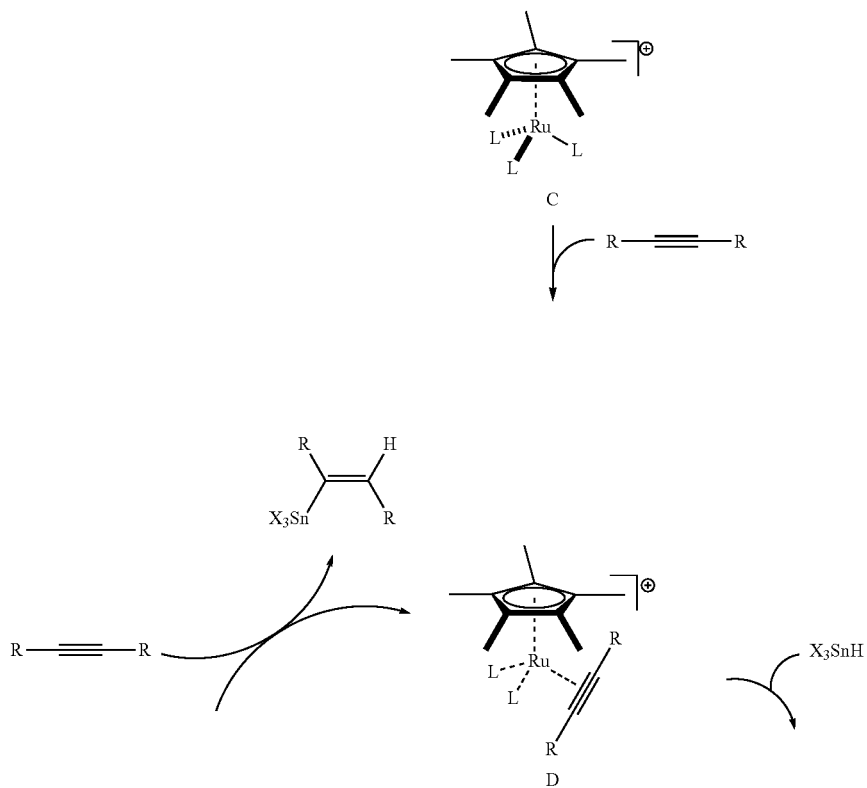

-continued

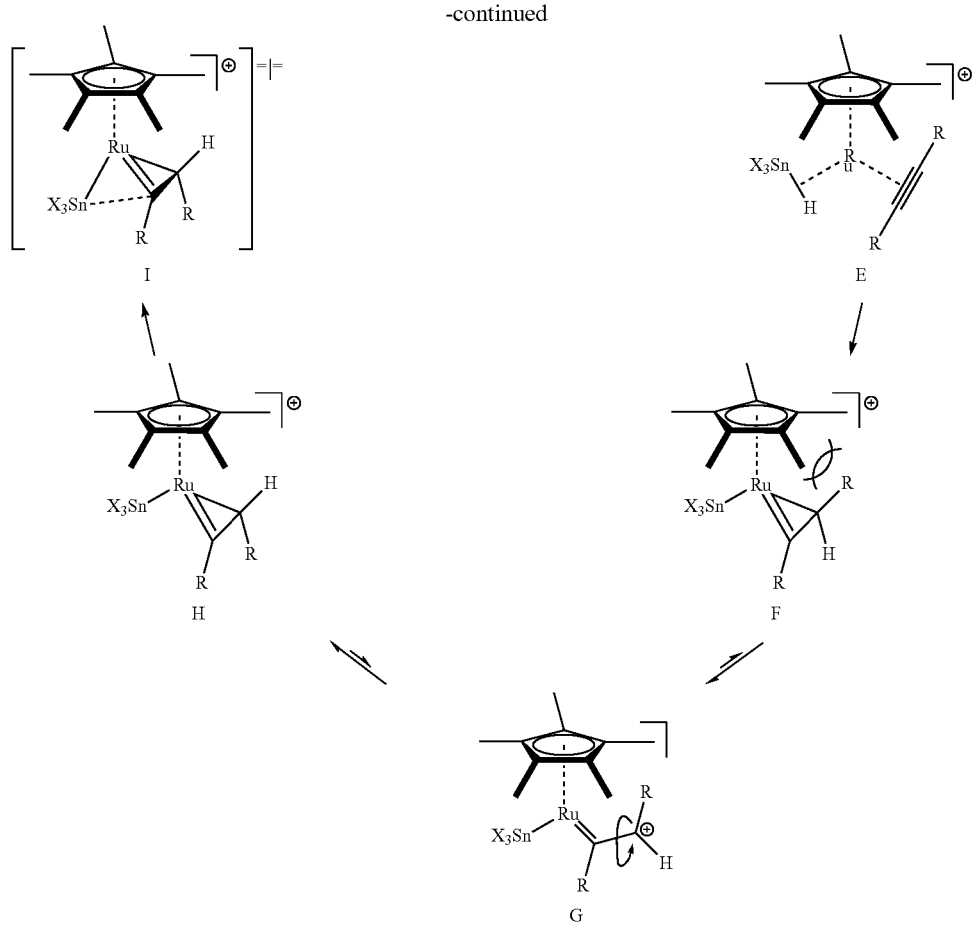

Although it is premature at this stage to draw a conclusive mechanistic picture, the basic features of the trans-selective hydrostannation can be rationalized as shown in Scheme 2.

The inventors assume that binding of an alkyne to the electrophilic metal center of C subsequently favors coordination of the tin hydride rather than of a second alkyne on electronic grounds. In the resulting loaded complex E, the acetylene moiety is supposed to function as a four-electron donor, which explains why alkenes do not react under the chosen conditions. This bonding situation, in turn, facilitates an inner-sphere nucleophilic delivery of the hydride with formation of a metallacyclopropene F ($\eta^2$-vinyl complex) without prior generation of a discrete Ru—H species. It is very well precedented that the substituents at the β-carbon atom of such complexes are configurationally labile and can easily swap places via a $\eta^2 \rightarrow \eta^1 \rightarrow \eta^2$ hapticity change (Frohnapfel, D. S. et al., Coord. Chem. Rev. 206-207, 199-235 (2000)). As they are approximately orthogonal to the plane of the metallacyclopropene, the sheer size of the Cp* ring will exert a massive influence on the stereochemical outcome. As a consequence, isomer H, in which the hydrogen rather than the R group is oriented towards the bulky lid, will be largely favored over F. This decisive steric factor loses weight if the lateral methyl groups of the Cp* ring are formally removed and [CpRu]-based catalysts are used. The trajectory of the ensuing reductive elimination places the tin entity anti to the hydrogen atom and hence leads to the formation of an E-configured alkenylstannane product. It is emphasized, however, that it cannot be excluded that the order of transfer of hydrogen and tin to the alkyne substrate could also be reversed, with the tin residue being delivered prior to delivery of the hydrogen atom.

It has been mentioned above that the proper choice of catalyst can impart high levels of regioselectivity on the trans-hydrostannation of unsymmetrical alkynes. This effect of matching substrate and catalyst is broadly applicable. Further representative examples are shown in Table 3. Excellent results are usually obtained when substrates containing an acidic or slightly acidic proton in proximity to the triple bond are reacted with the appropriate tin hydride in the presence of a Cp*Ru-catalyst containing a chloride substituent. Preferred catalysts are [Cp*Ru(cod)Cl] (5), [Cp*RuCl$_2$]$_n$ (7), or [(Cp*RuCl)$_4$] (8) (prepared according to: P. J. Fagan et al., Organometallics 1990, 9, 1843). This strong directing effect might stem from a pre-orientation of substrate and/or tin hydride within the coordination sphere of the catalyst and/or from a change in mechanism.

This effect is particularly pronounced for propargylic alcohols, independent of whether their alcoholic function is primary, secondary or tertiary; increasing steric demand does not seem to override this pronounced bias, as is often the case in hydrostannations catalyzed by other transition metals. Comparison of Tab. 3, entries 7 and 8 confirms that the largely improved regioselectivity is intimately related with the presence of an unprotected hydroxyl group and not merely caused by dipolar interactions in the transition state. Even if the —OH group is located at a homopropargylic or bis-homopropargylic position, appreciable regioselectivity can be harnessed (Tab. 3, entries 12, 13, 20, 21, 22).

Likewise, amides and sulfonamides at a propargylic (entry 14) or homopropargylic position (entries 31-34) exert a strong directing effect in the presence of a chloride-containing ruthenium catalyst such as 7 or 8. Tab. 3, entries 31-34 even suggest that the level of regioselectivity is directly correlated with the acidity of —NH group of the amide or sulfonamide. The example shown in entry 30 demonstrates that a heterocyclic ring containing a protic site is also able to exert a strong directing effect.

Moreover, the effect extends to acetylene carboxylate derivatives. Hydrostannations in the presence of the cationic catalyst 3, albeit highly trans-selective, were regio-indiscriminative (Tab. 2, entry 11 and Tab. 3, entries 15, 17); in contrast, the use of complex 8 engenders a highly regioselective reaction at the proximal α-position of the acid (Tab. 3, entries 16, 19), whereas an acetylenic ester exhibits the opposite preference for stannylation at the distal β-site (entry 18). This dichotomy is obviously useful in preparative terms and distinguishes the current method from other transition metal-catalyzed hydrostannations, which tend to be α-selective even in the acetylenic ester series. It has been previously mentioned in this Patent application that the affinity of [Cp*Ru] to arenes, dienes, enynes or polyenes likely explains why substrates containing such functionalities are less reactive or even unreactive under the conditions shown in Table 2 of the current patent application. In contrast, several examples presented in Table 3 suggest that a protic functionality in proximity to a triple bond—in combination with a chloride containing ruthenium catalysts such as 5, 7 or 8—exerts a sufficiently strong activating effect (in addition to the effect on the regioselectivity of trans-hydrostannation), thus allowing such otherwise poorly reactive or even unreactive substrates to be trans-hydrostannylated with respectable to excellent yields and selectivities (Tab. 3, entries 25, 26, 27, 29).

This activating effect is also visible in the example shown in entry 35, in which a diyne substrate has been subjected to trans-hydrostannation. In this case, the triple bond next to the alcohol group reacts preferentially, while the distal triple bond remains largely unaffected. If one alkyne is terminal and another one is internal or silylated, even the cationic ruthenium complex [Cp*Ru(MeCN)$_3$]PF$_6$ (3) is capable of imposing site-selectivity on diyne substrates: it is the terminal alkyne which reacts with good to excellent selectivity. Representative examples for this ability to select amongst two alkynes are contained in the Experimental Section.

TABLE 3 trans-Hydrostannation of unsymmetrical alkynes containing protic functionalities in proximity to the triple bonds.[a]

| Entry | Major Product | Catalyst[b] | α:β [c] | Z:E [c] | Yield [%] |
|---|---|---|---|---|---|
| 1 | | 3 | 74:26 | 99:1 (α) | 91 |
| 2 | | 5 | 97:3 | 99:1 (α) | 73 |
| 3 | | 7 | 98:2 | 99:1 (α) | 88 [d] |
| 4 | | 8 | 98:2 | 99:1 (α) | 81 |
| 5 | | 3 | 60:40 | 99:1 (α) | quant. [e] |
| 6 | | 8 | 95:5 | 99:1 (α) | 83 [f] |
| 7 | | 8 | 98:2 | 99:1 (α) | 84 (R = H)[g] |
| 8 | | 8 | 75:25 | 94:6 (α) | 86 (R = Ac) |
| 9 | | 8 | 97:3 | 99:1 (α) | 77 (R = H) |
| 10 | | 8 | 98:2 | 99:1 (α) | 72 (R = butyl) |
| 11 | | 8 | 99:1 | 99:1 (α) | 97 |
| 12 | | 8 | 81:19 | 95:5 (α) | 81 |

TABLE 3-continued trans-Hydrostannation of unsymmetrical alkynes containing protic functionalities in proximity to the triple bonds.[a]

| Entry | Major Product | Catalyst[b] | α:β [c] | Z:E [c] | Yield [%] |
|---|---|---|---|---|---|
| 13 | (structure with SnBu₃, OH) | 8 | 83:17 | 99:1 (α) | 86 |
| 14 | (structure with SnBu₃, NHTs) | 8 | 99:1 | 99:1 (α) | 90 |
| 15 | (structure with SnBu₃, COOH) | 3 | 50:50 | 91:9 (β) | 77 |
| 16 | | 8 | 90:10 | 96:4 (α) | 87[d,h] |
| 17 | (structure with Bu₃Sn, COOEt) | 3 | 40:60 | 99:1 (β) | 90 |
| 18 | | 8[i] | 6:94 | 95:5 (β) | 71[i,j] |
| 19 | (structure with SnBu₃, COOH) | 8 | 93:7 | 99:1 (α) | 87[h,k] |
| 20 | (structure with HO, SnBu₃) | 8 | 94:6 | 98:2 | 83% |
| 21 | (cyclopentane with HO, SnBu₃) | 8 | 96:4 | 99:1 | 88% |
| 22 | (structure with SnBu₃, OH) | 7 | 96:4 | 99:1 | 83% |
| 23 | (macrocyclic lactone with SnBu₃, OH) | 7 | 95:5 | 96:4 | 86% |
| 24 | (structure with OH, Bu₃Sn, OEt) | 8 | 97:3 | 99:1 | 66% |

TABLE 3-continued
trans-Hydrostannation of unsymmetrical alkynes containing protic functionalities in proximity to the triple bonds.[a]
| Entry | Major Product | Catalyst[b] | α:β [c] | Z:E [c] | Yield [%] |
|---|---|---|---|---|---|
| 25 | 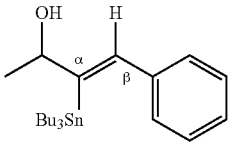 | 8 | 99:1 | 99:1 | 84% |
| 26 | 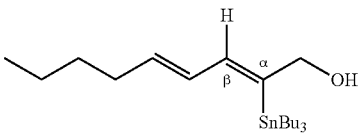 | 8 | 99:1 | 87:13 | 60%[j] |
| 27 | 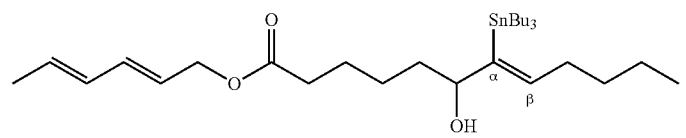 | 8 | 96:4 | 99:1 | 37% |
| 28 | 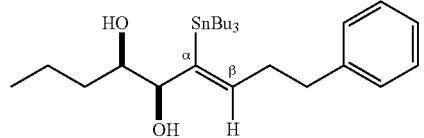 | 8 | 98:2 | 99:1 | 92% |
| 29 | 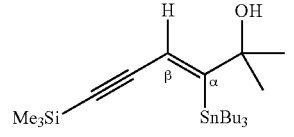 | 8 | 99:1 | 99:1 | 55% |
| 30 | 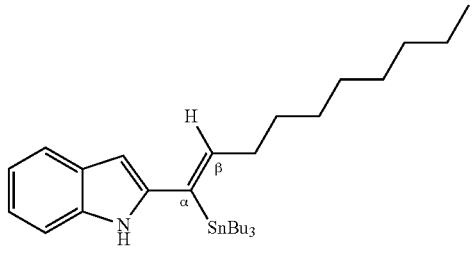 | 8 | 95:5 | 99:1 | 81% |
| 31 | 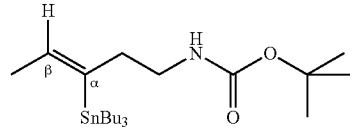 | 7 | 77:23 | 96:1 | 92% |
| 32 | 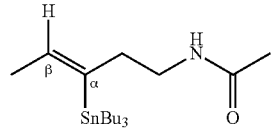 | 7 | 87:13 | 94:6 | 98% |
| 33 | 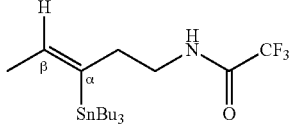 | 7 | 95:5 | 95:5 | 90% |

TABLE 3-continued trans-Hydrostannation of unsymmetrical alkynes containing protic functionalities in proximity to the triple bonds.[a]

| Entry | Major Product | Catalyst[b] | α:β [c] | Z:E [c] | Yield [%] |
|---|---|---|---|---|---|
| 34 | (structure with SnBu₃, NHSO₂CF₃) | 7 | 100:0 | 91:9 | 78% |
| 35 | (structure with OH, Bu₃Sn, (CH₂)₈, alkyne) | 8 | n.d. | 99:1 | 55% |

[a] unless stated otherwise, all reactions were performed on 0.1-0.2 mmol scale by adding Bu₃SnH (1.1 equiv.) over ≈5 min to a solution of the substrate and the respective catalyst in CH₂Cl₂ (0.2M) under Ar;
[b] using 3 or 5 or 7 (5 mol %), or 8 (1.25 mol %);
[c] ratio is the crude product, as determined by ¹H NMR;
α refers to the compound bearing the tin residue proximal to the protic site, whereas β refers to the compound bearing the tin residue distal to the protic site;
[d] ≥1 mmol scale;
[e] conversion (¹H NMR);
[f] 2.1 mmol scale;
[g] small amounts of the corresponding ketone were also found;
[h] using 1.0 eq. of Bu₃SnH;
[i] the substrate was added over 1.5 h;
[j] the yield refers to the pure major isomer after flash chromatography;
[k] 0.6 mmol scale;
n.d. = not determined Thus, by the present invention, the inventors have shown that simple ruthenium catalysts, most notably complexes [Cp*Ru(MeCN)₃]PF₆, [Cp*Ru(cod)Cl], [Cp*RuCl₂]ₙ, or [(Cp*RuCl)₄] (Cp*=η⁵-C₅Me₅), some of which are commercially available, allow the fundamental and largely unchallenged rule of suprafacial delivery of hydrogen and tin to the same π-face of a given starting material (cis-addition mode) to be broken for alkynes as the substrates. Moreover, the present invention is superior to the trans-hydrostannation of alkynes based on the use of catalytic or stoichiometric amounts of strong Lewis acids such as ZrCl₄, HfCl₄ or fluorinated borane derivatives, notably with regard to the functional group tolerance as well as the user-friendliness. The searching of libraries of matching candidates of alkyne, ruthenium catalyst and tin hydride provides the simple means of finding the best system for a given transition Ru-catalyzed conversion. This procedure is simple and can be performed rapidly by standard laboratory techniques or, alternatively, with modern instruments which are customary in combinatorial catalysis. The resulting trans-hydrostannation opens a practical new gateway to Z-configured alkenyltin derivatives which could previously only be made by indirect routes or by radical processes, which however often lead to mixtures of isomers or to different regioisomers. The inventors expect this stereo-complementary methodology to add another dimension to the uniquely prolific field of organotin chemistry. The inventive alkenyltin derivatives can be used for further synthesis of, for example, drug compounds or drug candidates, natural products, fine chemicals, agrochemicals, polymers, liquid crystals, fragrances, flavors, cosmetic ingredients, sun protective agents. Furthermore, they can be used for the preparation of compound libraries by combinatorial or parallel synthesis.

The invention is further illustrated by the general method for trans-hydrostannation as shown in Example 1 and further exemplified in the subsequent Examples 2 to 42 for various products of the trans-hydrostannation of alkynes.

EXAMPLE 1

(Z)-Tributyl(dec-5-en-5-yl)stannane

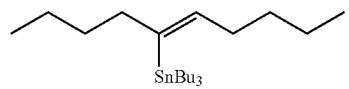

Tributyltin hydride (0.99 mL, 3.68 mmol, 1.05 equiv) was added dropwise under Argon over 6 min to a stirred solution of and 5-decyne (0.63 mL, 3.5 mmol, 1.0 equiv) and [Cp*Ru(CH₃CN)₃]PF₆ (88.2 mg, 0.175 mmol, 0.05 equiv) in dry CH₂Cl₂ (17.5 mL) at ambient temperature. Once the addition was complete, stirring was continued for another 15 min before the solvent was evaporated. The residue was purified by filtration through a short pad of silica using hexane as the eluent. Evaporation of the product-containing fractions afforded (Z)-tri butyl(dec-5-en-5-yl)stannane as a colorless oil (1.42 g, 94%) (Z/E>99:1 (NMR)). ¹H NMR (400 MHz, CDCl₃): δ=5.98 (tt, J=7.1, 1.2 Hz, 1H), 2.25-2.05 (m, 2H), 2.03-1.91 (m, 2H), 1.59-1.39 (m, 6H), 1.39-1.22 (m, 14H), 1.00-0.80 (m, 21H); ¹³C NMR (101 MHz, CDCl₃): δ=143.4, 140.8, 40.6, 34.9, 33.1, 32.8, 29.4, 27.6, 22.7, 22.4, 14.3, 14.2, 13.8, 10.4; IR ($v_{max}$/cm⁻¹) 2955, 2922, 2872, 2854, 1463, 1377, 1071.

EXAMPLE 2

Diethyl 2-(tributylstannyl)fumarate

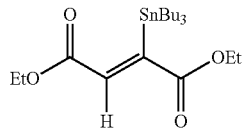

Prepared analogously as a pale yellow oil (63.8 mg, 69%) (Z/E>99:1 (NMR)). $^1$H NMR (400 MHz, CDCl$_3$): δ=6.82 (s, 1H), 4.22 (q, J=7.1 Hz, 2H), 4.20 (q, J=7.2 Hz, 2H), 1.58-1.37 (m, 6H), 1.37-1.24 (m, 12H), 1.14-0.94 (m, 6H), 0.88 (t, J=7.3 Hz, 9H); $^{13}$C NMR (101 MHz, CDCl$_3$): δ=172.5, 167.4, 161.7, 134.8, 61.19, 61.15, 29.1, 27.4, 14.43, 14.36, 13.8, 12.1; IR ($v_{max}$/cm$^{-1}$) 2956, 2921, 2872, 2853, 1709, 1463, 1367, 1313, 1193, 1036; ESI-MS calcd for C$_{20}$H$_{38}$O$_4$SnNa (M+Na$^+$) 485.16836. found 485.16858.

EXAMPLE 3

(Z)-2-(Tributylstannyl)but-2-ene-1,4-diyl diacetate

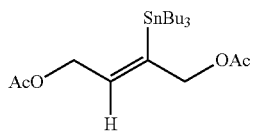

Prepared analogously as a colorless oil (73.8 mg, 80%) (Z/E=99:1 (NMR)); $^1$H NMR (400 MHz, CDCl$_3$): δ=6.39 (tt, J=6.9, 1.6 Hz, 1H), 4.74-4.63 (m, 2H), 4.56-4.47 (m, 2H), 2.07 (s, 3H), 2.06 (s, 3H), 1.57-1.39 (m, 6H), 1.38-1.25 (m, 6H), 1.03-0.93 (m, 6H), 0.89 (t, J=7.3 Hz, 9H); $^{13}$C NMR (101 MHz, CDCl$_3$): δ=170.8, 170.6, 145.6, 135.6, 71.1, 65.7, 29.1, 27.4, 21.10, 21.08, 13.8, 10.6; IR ($v_{max}$/cm$^{-1}$) 2956, 2925, 2872, 2853, 1740, 1459, 1376, 1217, 1077, 1021; ESI-MS calcd for C$_{20}$H$_{38}$O$_4$SnNa (M+Na$^+$) 485.16836. found 485.16855.

EXAMPLE 4

(Z)-Tributyl(1,12-dibromododec-6-en-6-yl)stannane

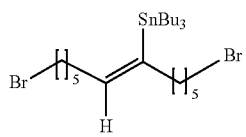

Prepared analogously as a colorless oil (49.1 mg, 80%). (Z/E=97:3 (NMR)); $^1$H NMR (400 MHz, CDCl$_3$): δ=5.97 (tt, J=7.2, 1.2 Hz, 1H), 3.40 (td, J=6.8, 3.3 Hz, 4H), 2.26-2.06 (m, 2H), 2.04-1.93 (m, 2H), 1.93-1.78 (m, 4H), 1.57-1.37 (m, 12H), 1.37-1.25 (m, 8H), 0.99-0.80 (m, 15H); $^{13}$C NMR (101 MHz, CDCl$_3$): δ=143.6, 140.6, 40.6, 34.9, 34.1, 33.9, 33.0, 32.9, 29.9, 29.6, 29.4, 28.2, 27.9, 27.6, 13.7, 10.5; IR ($v_{max}$/cm$^{-1}$) 2955, 2924, 2870, 2853, 1459, 1264, 1071.

EXAMPLE 5

(Z)-3-(Tributylstannyl)hex-3-ene-1,6-diyl bis(4-methylbenzene-sulfonate)

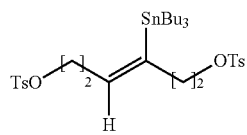

Prepared analogously as a colorless oil (69.6 mg, 98%) (Z/E=99:1 (NMR)); $^1$H NMR (400 MHz, CDCl$_3$): δ=7.77 (dq, J=8.5, 2.1 Hz, 4H), 7.39-7.31 (m, 4H), 5.85 (tt, J=7.1, 1.3 Hz, 1H), 3.95 (t, J=6.9 Hz, 2H), 3.88 (t, J=7.4 Hz, 2H), 2.52-2.38 (m, 8H), 2.32 (q, J=7.0 Hz, 2H), 1.45-1.31 (m, 6H), 1.32-1.19 (m, 6H), 0.86 (t, J=7.3 Hz, 9H), 0.84-0.79 (m, 6H); $^{13}$C NMR (101 MHz, CDCl$_3$): δ=145.0, 144.9, 142.2, 137.8, 133.3, 133.2, 130.01, 129.99, 128.1, 128.0, 69.9, 69.6, 39.3, 34.5, 29.2, 27.4, 21.8, 13.8, 10.3; IR ($v_{max}$/cm$^{-1}$) 2955, 2924, 2871, 2853, 1598, 1463, 1360, 1188, 1174, 1097; ESI-MS calcd for C$_{32}$H$_{50}$O$_6$S$_2$SnNa (M+Na$^+$) 737.19623. found 737.19663.

EXAMPLE 6

(Z)-Tributyl(1,12-diazidododec-6-en-6-yl)stannane

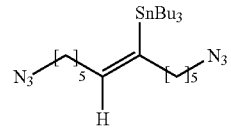

Prepared analogously as a yellow oil (30.2 mg, 56%) (Z/E=98:2 (NMR)); $^1$H NMR (400 MHz, CDCl$_3$) δ=5.97 (tt, J=7.1, 1.3 Hz, 1H), 3.31-3.22 (m, 4H), 2.27-2.05 (m, 2H), 2.05-1.91 (m, 2H), 1.67-1.54 (m, 4H), 1.53-1.42 (m, 6H), 1.42-1.36 (m, 4H), 1.36-1.25 (m, 10H), 0.99-0.80 (m, 15H); $^{13}$C NMR (101 MHz, CDCl$_3$) δ=143.6, 140.6, 51.64, 51.57, 40.6, 34.9, 30.2, 30.0, 29.4, 29.0, 28.9, 27.6, 26.7, 26.4, 13.8, 10.4; IR ($v_{max}$/cm$^{-1}$) 2954, 2925, 2870, 2854, 2090, 1457, 1347, 1256, 1072.

EXAMPLE 7

(Z)-9-(Tributylstannyl)octadec-9-ene-2,17-dione

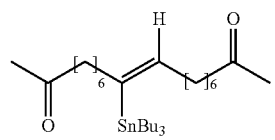

Prepared analogously as a colorless oil (53.3 mg, 94%) (Z/E=99:1 (NMR)); $^1$H NMR (400 MHz, CDCl$_3$) δ=5.94 (tt, J=7.1, 1.3 Hz, 1H), 2.40 (td, J=7.5, 1.8 Hz, 4H), 2.18-2.03 (m, 2H), 2.12 (s, 6H), 1.99-1.91 (m, 2H), 1.61-1.51 (m, 4H), 1.50-1.41 (m, 6H), 1.37-1.21 (m, 18H), 0.95-0.79 (m, 15H); $^{13}$C NMR (101 MHz, CDCl$_3$) δ=209.4, 209.3, 143.5, 140.7, 44.0, 43.9, 40.8, 35.1, 30.7, 30.3, 29.97, 29.95, 29.41, 29.39, 29.36, 29.25, 29.1, 27.6, 24.1, 24.0, 13.8, 10.4; IR ($v_{max}$/cm$^{-1}$) 2953, 2923, 2870, 2852, 1717, 1458, 1417, 1357, 1161, 1071; ESI-MS calcd for $C_{30}H_{59}O_2Sn$ (M+H$^+$) 571.35364. found 571.35409.

EXAMPLE 8

Ethyl (Z)-2-(tributylstannyl)but-2-enoate and Ethyl (Z)-3-(tributylstannyl)but-2-enoate

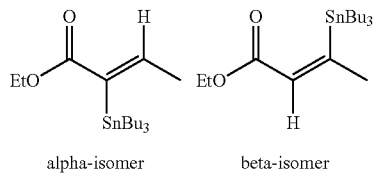

alpha-isomer    beta-isomer

Prepared analogously as a mixture of regioisomers (α/β=1/1.5); colorless oil (72.8 mg, 90%). The Z/E ratio (NMR) was found to be 99/1 for the β-isomer and >99/1 for the α-isomer. The regioisomers can be separated by flash chromatography (SiO$_2$) using hexanes/EtOAc (1/0→50/1→5/1) as the eluent.

Characteristic data of the β-Isomer: $^1$H NMR (400 MHz, CDCl$_3$): δ=6.41 (q, J=1.7 Hz, 1H), 4.17 (q, J=7.1 Hz, 2H), 2.13 (d, J=1.7 Hz, 3H), 1.54-1.37 (m, 6H), 1.36-1.23 (m, 9H), 1.07-0.91 (m, 6H), 0.88 (t, J=7.3 Hz, 9H); $^{13}$C NMR (101 MHz, CDCl$_3$): δ=171.7, 167.9, 129.4, 60.2, 29.4, 27.6, 27.6, 14.5, 13.9, 11.1; IR ($v_{max}$/cm$^{-1}$) 2955, 2920, 2871, 2852, 1701, 1600, 1463, 1368, 1315, 1191, 1099, 1043; ESI-MS calcd for $C_{18}H_{36}O_2SnNa$ (M+Na$^+$) 427.16288. found 427.16337.

Characteristic data of the α-Isomer: $^1$H NMR (400 MHz, CDCl$_3$): δ=7.46 (q, J=6.9 Hz, 1H), 4.15 (q, J=7.1 Hz, 2H), 1.91-1.85 (m, 3H), 1.56-1.42 (m, 6H), 1.37-1.24 (m, 9H), 1.09-0.92 (m, 6H), 0.88 (t, J=7.3 Hz, 9H). $^{13}$C NMR (101 MHz, CDCl$_3$): δ=171.7, 152.3, 137.4, 60.5, 29.2, 27.4, 19.7, 14.5, 13.8, 11.5.

EXAMPLE 9

(Z)-4-(Tributylstannyl)-4-(trimethylsilyl)but-3-en-1-ol

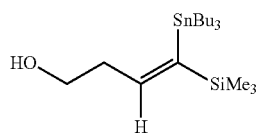

Prepared analogously as a mixture of regioisomers (α/β=96/4); colorless oil (35.5 mg, 82%). The Z/E ratio (NMR) was found to be >99/1 for the α-isomer. Characteristic data of the α-Isomer: $^1$H NMR (400 MHz, CDCl$_3$): δ=6.72 (t, J=6.6 Hz, 1H), 3.73 (t, J=6.6 Hz, 2H), 2.42 (q, J=6.6 Hz, 2H), 1.59-1.38 (m, 6H), 1.38-1.25 (m, 7H), 1.04-0.92 (m, 6H), 0.89 (t, J=7.3 Hz, 9H), 0.05 (s, 9H); $^{13}$C NMR (101 MHz, CDCl$_3$): δ=150.8, 148.0, 62.3, 42.5, 29.4, 27.6, 13.8, 11.5, −0.1; IR ($v_{max}$/cm$^{-1}$) 3310, 2954, 2923, 2871, 2854, 1571, 1463, 1376, 1245, 1046; ESI-MS calcd for $C_{19}H_{43}OSiSn$ (M+H$^+$) 435.21045. found 435.21003.

EXAMPLE 10

(Z)-4-(Tributylstannyl)-4-(trimethylsilyl)but-3-en-1-yl 4-methoxybenzoate

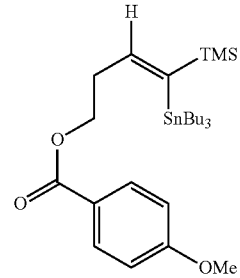

Prepared analogously as a mixture of regioisomers (α/β=96/4); colorless oil (111.7 mg, 98%); The Z/E ratio (NMR) was found to be >99/1 for the α-isomer. Characteristic data of the α-Isomer: $^1$H NMR (400 MHz, CDCl$_3$) δ=8.05-7.95 (m, 2H), 6.95-6.88 (m, 2H), 6.78 (t, J=6.4 Hz, 1H), 4.37 (t, J=6.7 Hz, 2H), 3.86 (s, 3H), 2.65-2.52 (m, 2H), 1.57-1.38 (m, 6H), 1.38-1.25 (m, 6H), 1.06-0.92 (m, 6H), 0.88 (t, J=7.3 Hz, 9H), 0.06 (s, 9H); $^{13}$C NMR (101 MHz, CDCl$_3$) δ=166.4, 163.5, 150.3, 147.4, 131.7, 123.0, 113.7, 63.9, 55.6, 38.5, 29.4, 27.5, 13.8, 11.4, −0.1; IR ($v_{max}$/cm$^{-1}$) 2954, 2926, 2871, 2853, 1715, 1607, 1511, 1459, 1273, 1254, 1166, 1099, 1033.

EXAMPLE 11

(Z)-(5-Chloro-5-(tributylstannyl)pent-4-en-1-yl)triethylsilane

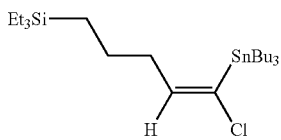

Prepared analogously as a colorless oil (α/β>99:1) (47.6 mg, 94%) (Z/E>99:1 (NMR)); $^1$H NMR (400 MHz, CDCl$_3$) δ=6.65 (t, J=6.6 Hz, 1H), 3.55 (t, J=6.7 Hz, 2H), 2.36-2.23 (m, 2H), 1.96-1.85 (m, 2H), 1.57-1.39 (m, 6H), 1.39-1.25 (m, 6H), 1.02-0.79 (m, 24H), 0.56 (q, J=7.9 Hz, 6H); $^{13}$C NMR (101 MHz, CDCl$_3$) δ=155.3, 141.6, 44.7, 36.9, 32.8, 29.4, 27.6, 13.8, 11.6, 7.7, 3.9; IR ($v_{max}$/cm$^{-1}$) 2953, 2927, 2872, 2854, 1570, 1458, 1376, 1235, 1071, 1003.

EXAMPLE 12

Methyl 5-(tri butylstannyl)hex-5-enoate

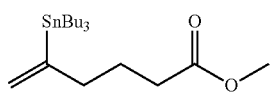

A solution containing methyl hex-5-ynoate (26 µL, 0.20 mmol, 1.0 equiv) and tributyltin hydride (0.22 mmol, 59 µL, 1.1 equiv) in CH$_2$Cl$_2$ (0.5 mL) was added dropwise over 12 min to a stirred solution of [Cp*Ru(CH$_3$CN)$_3$]PF$_6$ (5.0 mg, 10 µmol, 0.05 equiv) in CH$_2$Cl$_2$ (0.5 mL) under argon. Once the addition was complete, the mixture was stirred for another 15 min before all volatile materials were evaporated. The residue was passed through a short plug of silica, eluting with hexanes/EtOAc (20:1) to give the title compound as a mixture of regioisomers (terminal:internal=3:97) as a colorless oil (60.5 mg, 73%). Data of the major isomer: $^1$H NMR (400 MHz, CDCl$_3$) δ=5.67 (dt, J=2.8, 1.5 Hz, 1H), 5.14 (dt, J=2.3, 1.0 Hz, 1H), 3.66 (s, 3H), 2.37-2.20 (m, 4H), 1.77-1.66 (m, 2H), 1.58-1.38 (m, 6H), 1.36-1.25 (m, 6H), 1.00-0.78 (m, 15H); $^{13}$C NMR (101 MHz, CDCl$_3$) δ=174.1, 154.4, 125.9, 51.6, 40.6, 33.6, 29.3, 27.5, 24.7, 13.8, 9.7; IR (v$_{max}$/cm$^{-1}$) 2955, 2925, 2872, 2852, 1742, 1457, 1436, 1376, 1245, 1222, 1193, 1170, 1072.

EXAMPLE 13

(Z)-3-(Tributylstannyl)pent-3-en-2-ol

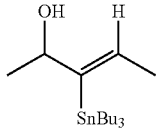

Tributyltin hydride (1.1 mmol, 0.30 mL, 1.1 equiv) was added dropwise over 5 min to a stirred solution of [Cp*RuCl$_2$]$_n$ (n≥2) (prepared according to: N. Oshima et al., Chem. Lett. 1984, 1161) (15.4 mg, 0.025 mmol, 0.025 equiv) and 3-pentyn-2-ol (93 µL, 1.0 mmol, 1.0 equiv) in anhydrous CH$_2$Cl$_2$ (5.0 mL, 0.2 M) under argon. The resulting mixture was stirred for 15 min before all volatile materials were evaporated. The residue was loaded on top of a flash column packed with SiO$_2$ and the product eluted with hexane/EtOAc (50/1→30/1) to give the title compound as a pale yellow oil (329 mg, 88%, α/β isomer=98/2). The Z/E ratio was found to be >99/1 for the α-isomer. Characteristic data of the α-Isomer: $^1$H NMR (400 MHz, CDCl$_3$): δ=6.27 (qd, J=6.7, 1.2 Hz, 1H), 4.35 (qd, J=6.3, 3.1 Hz, 1H), 1.76-1.69 (m, 3H), 1.60-1.40 (m, 6H), 1.39-1.28 (m, 7H), 1.21 (d, J=6.3 Hz, 3H), 1.07-0.92 (m, 6H), 0.89 (t, J=7.3 Hz, 9H); $^{13}$C NMR (101 MHz, CDCl$_3$): δ=150.5, 133.6, 75.8, 29.4, 27.5, 24.4, 19.3, 13.8, 11.0; IR (v$_{max}$/cm$^{-1}$) 3345, 2955, 2922, 2871, 2853, 1621, 1456, 1375, 1289, 1248, 1069.

EXAMPLE 14

(Z)-2-(Tributylstannyl)pent-2-en-1-ol

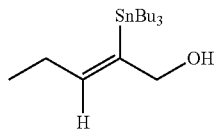

Prepared analogously using [(Cp*RuCl)$_4$] (1.25 mol %) as the catalyst; colorless oil (670 mg, 83%) (α/β=95/5) (Z/E=99:1 for the major isomer (NMR)); $^1$H NMR (400 MHz, CDCl$_3$): δ=6.21 (tt, J=7.1, 1.4, J$_{Sn-H}$=122.9 Hz, 1H), 4.25-4.08 (m, 2H), 2.10-1.98 (m, 2H), 1.59-1.39 (m, 6H), 1.38-1.25 (m, 6H), 1.20 (t, J=5.9 Hz, 1H), 1.06-0.92 (m, 9H), 0.89 (t, J=7.3 Hz, 9H); $^{13}$C NMR (101 MHz, CDCl$_3$): δ=143.6, 142.6, 70.6, 29.4, 27.9, 27.5, 14.6, 13.8, 10.4; $^{119}$Sn NMR (112 MHz, CDCl$_3$): δ=−52.3 ppm; IR (film, cm$^{-1}$): ṽ=3316, 2956, 2923, 2871, 2851, 1622, 1459, 1418, 1376, 1291, 1148, 1080, 1000; ESI-MS calcd for C$_{17}$H$_{35}$OSn (M−H$^-$) 375.17147. found 375.17155.

EXAMPLE 15

(Z)-3-(Tributylstannyl)hex-3-en-2-ol

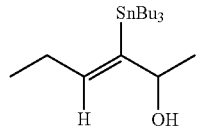

Prepared analogously using [(Cp*RuCl)$_4$] (1.25 mol %) as the catalyst; colorless oil (65.5 mg, 84%) (α/β=98/2) (Z/E=99:1 for the major isomer (NMR)); $^1$H NMR (400 MHz, CDCl$_3$): δ=6.15 (td, J=7.2, 1.1, J$_{Sn-H}$=125.7 Hz, 1H), 4.34 (qdd, J=6.4, 3.4, 1.0 Hz, 1H), 2.09-1.94 (m, 2H), 1.59-1.39 (m, 6H), 1.38-1.26 (m, 7H), 1.22 (d, J=6.3 Hz, 3H), 1.09-0.92 (m, 9H), 0.89 (t, J=7.3 Hz, 9H); $^{13}$C NMR (101 MHz, CDCl$_3$): δ=148.4, 141.2, 75.7, 29.4, 27.6, 27.5, 24.4, 14.6, 13.8, 11.2; $^{119}$Sn NMR (112 MHz, CDCl$_3$): δ=−53.8 ppm; IR (film, cm$^{-1}$): ṽ=3354, 2957, 2923, 2871, 2853, 1619, 1458, 1376, 1287, 1247, 1149, 1115, 1070, 1005; ESI-MS calcd for C$_{18}$H$_{37}$OSn (M−H$^-$) 389.18712. found 389.18728.

EXAMPLE 16

(Z)-3-(Tributylstannyl)hex-3-en-2-yl acetate

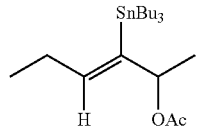

Prepared analogously using [(Cp*RuCl)$_4$] (1.25 mol %) as the catalyst; colorless oil (73.8 mg, 86%) (α/β=75:25) (Z/E=94:6 for the major isomer (NMR)); $^1$H NMR (400 MHz, CDCl$_3$): δ=6.18 (td, J=7.2, 1.0, J$_{Sn-H}$=122.3 Hz, 1H), 5.49-5.28 (m, 1H), 2.08-1.94 (m, 2H), 2.00 (s, 3H), 1.59-1.38 (m, 6H), 1.38-1.27 (m, 6H), 1.25 (d, J=6.4 Hz, 3H), 1.05-0.85 (m, 18H); $^{13}$C NMR (101 MHz, CDCl$_3$): δ=170.2, 151.1, 143.5, 78.6, 29.3, 27.54, 27.50, 22.1, 21.7, 14.4, 13.8, 11.1; $^{119}$Sn NMR (112 MHz, CDCl$_3$): δ=−52.4 ppm; IR (film, cm$^{-1}$): ṽ=2957, 2926, 2871, 2854, 1737, 1457, 1368, 1235, 1126, 1070, 1041, 1012; ESI-MS calcd for C$_{20}$H$_{40}$O$_2$SnNa (M+Na$^+$) 455.19418. found 455.19459.

EXAMPLE 17

(2Z,7Z)-3-(Tributylstannyl)trideca-2,7-dien-4-ol

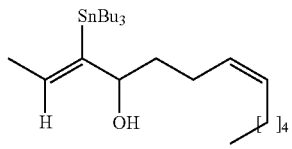

Prepared analogously using [(Cp*RuCl)$_4$] (1.25 mol %) as the catalyst; colorless oil (69.5 mg, 72%) (α/β=98:2) (Z/E=99:1 for the major isomer (NMR)); $^1$H NMR (400 MHz, CDCl$_3$): δ=6.25 (qd, J=6.6, 1.1, J$_{Sn-H}$=125.5 Hz, 1H), 5.44-5.30 (m, 2H), 4.13 (td, J=6.7, 3.1 Hz, 1H), 2.16-1.95 (m, 4H), 1.74 (d, J=6.5 Hz, 3H), 1.60-1.42 (m, 8H), 1.41 (d, J=3.2 Hz, 1H), 1.39-1.23 (m, 12H), 1.08-0.93 (m, 6H), 0.92-0.84 (m, 12H); $^{13}$C NMR (101 MHz, CDCl$_3$): δ=149.3, 134.9, 130.7, 129.2, 80.0, 37.8, 31.7, 29.6, 29.4, 27.6, 27.4, 24.0, 22.8, 19.4, 14.2, 13.8, 11.1; $^{119}$Sn NMR (112 MHz, CDCl$_3$): δ=−55.6 ppm; IR (film, cm$^{-1}$): ṽ=3466, 3004, 2955, 2922, 2871, 2854, 1620, 1457, 1376, 1290, 1070, 1003; ESI-MS calcd for C$_{25}$H$_{49}$OSn (M−H$^-$) 485.28102. found 485.28128.

EXAMPLE 18

(Z)-3-(Tributylstannyl)octa-2,7-dien-4-ol

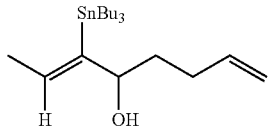

Prepared analogously using [(Cp*RuCl)$_4$] (1.25 mol %) as the catalyst; colorless oil (31.9 mg, 77%) (α/β=97:3) (Z/E=99:1 for the major isomer (NMR)); $^1$H NMR (400 MHz, CDCl$_3$): δ=6.25 (qd, J=6.7, 1.1, J$_{Sn-H}$=125.0 Hz, 1H), 5.83 (ddt, J=16.9, 10.2, 6.6 Hz, 1H), 5.02 (dq, J=17.1, 1.7 Hz, 1H), 4.96 (ddt, J=10.2, 2.3, 1.3 Hz, 1H), 4.24-4.02 (m, 1H), 2.19-1.96 (m, 2H), 1.74 (d, J=6.6 Hz, 3H), 1.66-1.42 (m, 8H), 1.41 (d, J=3.1 Hz, 1H), 1.39-1.22 (m, 6H), 1.09-0.69 (m, 6H), 0.89 (t, J=7.3 Hz, 9H); $^{13}$C NMR (101 MHz, CDCl$_3$): δ=149.3, 138.7, 135.0, 114.8, 79.9, 36.9, 30.4, 29.4, 27.6, 19.4, 13.8, 11.1; IR (film, cm$^{-1}$): ṽ=3429, 2956, 2922, 2871, 2853, 1641, 1620, 1456, 1376, 1260, 1071, 1046, 1016; ESI-MS calcd for C$_{20}$H$_{40}$OSnNa (M+Na$^+$) 439.19926. found 439.19957.

EXAMPLE 19

(Z)-1-(1-(Tributylstannyl)prop-1-en-1-yl)cyclohexan-1-ol

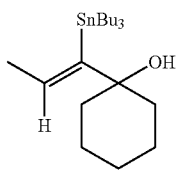

Prepared analogously using [(Cp*RuCl)$_4$] (1.25 mol %) as the catalyst; colorless oil (82.9 mg, 97%) (α/β=99:1) (Z/E=99:1 for the major isomer (NMR)); $^1$H NMR (400 MHz, CDCl$_3$): δ=6.24 (q, J=6.7, J$_{Sn-H}$=137.8 Hz, 1H), 1.74 (d, J=6.6 Hz, 3H), 1.69-1.53 (m, 6H), 1.53-1.38 (m, 9H), 1.38-1.27 (m, 6H), 1.26 (s, 1H), 1.22-1.07 (m, 1H), 1.06-0.86 (m, 6H), 0.89 (t, J=7.3 Hz, 9H); $^{13}$C NMR (101 MHz, CDCl$_3$): δ=155.3, 130.3, 75.7, 38.2, 29.4, 27.6, 25.7, 22.4, 19.3, 13.9, 12.4; $^{119}$Sn NMR (112 MHz, CDCl$_3$): δ=−55.7 ppm; IR (film, cm$^{-1}$): ṽ=3449, 2953, 2923, 2870, 2852, 1448, 1375, 1340, 1293, 1253, 1149, 1071; ESI-MS calcd for C$_{21}$H$_{42}$OSnNa (M+Na$^+$) 453.21492. found 453.21520.

EXAMPLE 20

(Z)-3-(Tributylstannyl)pent-3-en-1-ol

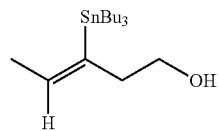

Prepared analogously using [(Cp*RuCl)$_4$] (1.25 mol %) as the catalyst; colorless oil (61.0 mg, 81%) (α/β=81:19) (Z/E=95:5 for the major isomer (NMR)); Data of the major isomer: $^1$H NMR (400 MHz, CDCl$_3$): δ=6.20 (qt, J=6.6, 1.3, J$_{Sn-H}$=129.6 Hz, 1H), 3.53 (q, J=6.1 Hz, 2H), 2.53-2.34 (m, 2H), 1.74 (dt, J=6.6, 0.9 Hz, 3H), 1.60-1.37 (m, 7H), 1.37-1.25 (m, 6H), 1.03-0.84 (m, 6H), 0.89 (t, J=7.3 Hz, 9H); $^{13}$C NMR (101 MHz, CDCl$_3$): δ=140.7, 138.6, 61.8, 43.6, 29.3, 27.5, 20.2, 13.8, 10.3; $^{119}$Sn NMR (112 MHz, CDCl$_3$): δ=−52.6 ppm; IR (film, cm$^{-1}$): ṽ=3319, 2955, 2922, 2871, 2852, 1620, 1462, 1418, 1376, 1291, 1181, 1040; ESI-MS calcd for C$_{17}$H$_{35}$OSn (M−H$^-$) 375.17147. found 375.17149.

EXAMPLE 21

(Z)-4-(Tributylstannyl)hex-4-en-1-ol

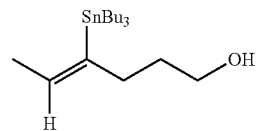

Prepared analogously using [(Cp*RuCl)$_4$] (1.25 mol %) as the catalyst; colorless oil (66.7 mg, 86%) (α/β=83:17) (Z/E=99:1 for the major isomer (NMR)); Data of the major isomer: $^1$H NMR (400 MHz, CDCl$_3$): δ=6.12 (qt, J=6.6, 1.3, J$_{Sn-H}$=132.7 Hz, 1H), 3.68-3.58 (m, 2H), 2.24 (ddt, J=8.7, 6.3, 1.2 Hz, 2H), 1.70 (dt, J=6.6, 1.0 Hz, 3H), 1.66-1.38 (m, 8H), 1.38-1.23 (m, 7H), 1.02-0.83 (m, 6H), 0.89 (t, J=7.3 Hz, 9H); $^{13}$C NMR (101 MHz, CDCl$_3$): δ=144.3, 135.0, 62.8, 37.1, 33.6, 29.4, 27.6, 20.0, 13.8, 10.3; $^{119}$Sn NMR (112 MHz, CDCl$_3$): δ=−53.0 ppm; IR (film, cm$^{-1}$): ṽ=3318, 2955, 2923, 2871, 2852, 1456, 1376, 1291, 1180, 1071, 1052, 1002; ESI-MS calcd for C$_{18}$H$_{37}$OSn (M−H$^-$) 389.18712. found 389.18720.

EXAMPLE 22

(Z)-4-Methyl-N-(3-(tributylstannyl)hex-3-en-2-yl)benzenesulfonamide

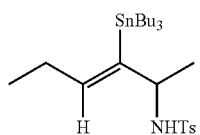

Prepared analogously using [(Cp*RuCl)$_4$] (1.25 mol %) as the catalyst; colorless oil (48.7 mg, 90%) (α/β=99:1) (Z/E=99:1 (NMR)); $^1$H NMR (400 MHz, CDCl$_3$): δ=7.74-7.66 (m, 2H), 7.30-7.22 (m, 2H), 5.93 (td, J=7.2, 1.0, J$_{Sn-H}$=120.7 Hz, 1H), 4.30 (d, J=6.3 Hz, 1H), 4.04-3.81 (m, 1H), 2.41 (s, 3H), 1.94-1.79 (m, 2H), 1.53-1.32 (m, 6H), 1.37-1.22 (m, 6H), 1.14 (d, J=6.7 Hz, 3H), 0.95-0.72 (m, 18H); $^{13}$C NMR (101 MHz, CDCl$_3$): δ=144.4, 143.2, 142.6, 138.2, 129.6, 127.5, 58.5, 29.3, 27.7, 27.5, 23.9, 21.6, 14.3, 13.8, 11.0; $^{119}$Sn NMR (112 MHz, CDCl$_3$): δ=−52.9 ppm; IR (film, cm$^{-1}$): ṽ=3268, 2956, 2924, 2871, 2853, 1456, 1417, 1374, 1325, 1160, 1094, 1071; ESI-MS calcd for C$_{25}$H$_{45}$NO$_2$SSnNa (M+Na$^+$) 566.20845. found 566.20883.

EXAMPLE 23

(Z)-2-(Tributylstannyl)hex-2-enoic acid

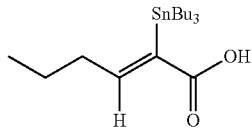

Prepared analogously using [(Cp*RuCl)$_4$] (1.25 mol %) as the catalyst and limiting the amount of Bu$_3$SnH to exactly 1 equivalent relative to the substrate; colorless oil (389 mg, 87%) (α/β=90:10) (Z/E=96:4 (NMR)); $^1$H NMR (500 MHz, CDCl$_3$): δ=7.50 (t, J=7.3, J$_{Sn-H}$=103 Hz, 1H), 2.17 (q, J=7.4 Hz, 2H), 1.56-1.41 (m, 8H), 1.37-1.27 (m, 6H), 1.09-0.85 (m, 18H); $^{13}$C NMR (126 MHz, CDCl$_3$): δ=177.5, 160.2, 135.8, 36.3, 29.2, 27.4, 22.5, 14.0, 13.8, 11.5; $^{119}$Sn NMR (186 MHz, CDCl$_3$): δ=−45.7 ppm; IR (film, cm$^{-1}$): ṽ=3042, 2956, 2922, 2871, 2853, 2621, 1662, 1600, 1462, 1404, 1377, 1272, 1073; ESI-MS calcd for C$_{18}$H$_{35}$O$_2$Sn (M−H$^-$) 403.16638. found 403.16671.

EXAMPLE 24

(Z)-4-(Tributylstannyl)hex-4-enoic acid

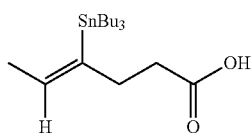

Prepared analogously using [(Cp*RuCl)$_4$] (1.25 mol %) as the catalyst and limiting the amount of Bu$_3$SnH to exactly 1 equivalent relative to the substrate; colorless oil (211 mg, 87%) (α/β=93:7) (Z/E=99:1 (NMR)). Data of the major isomer: $^1$H NMR (500 MHz, CDCl$_3$): δ=6.14 (qt, J=6.6, 1.4, J$_{Sn-H}$=129.8 Hz, 1H), 2.56-2.40 (m, 2H), 2.40-2.28 (m, 2H), 1.69 (dt, J=6.5, 1.0 Hz, 3H), 1.57-1.40 (m, 6H), 1.38-1.26 (m, 6H), 1.01-0.86 (m, 6H), 0.89 (t, J=7.3 Hz, 9H); $^{13}$C NMR (126 MHz, CDCl$_3$): δ=179.3, 142.3, 135.8, 35.3, 35.2, 29.4, 27.5, 20.1, 13.8, 10.2; $^{119}$Sn NMR (186 MHz, CDCl$_3$): δ=−51.5 ppm; IR (film, cm$^{-1}$): ṽ=3025, 2956, 2921, 2872, 2853, 1708, 1455, 1416, 1376, 1291, 1210, 1071, 1021; ESI-MS calcd for C$_{18}$H$_{35}$O$_2$Sn (M−H$^-$) 403.16639. found 403.16678. Note: this product is prone to proto-destannation (ca. 10% after 24 h, NMR).

EXAMPLE 25

(Z)-3-Methyl-4-(tributylstannyl)non-4-en-2-ol

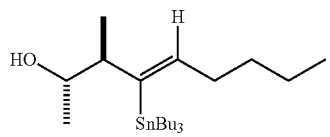

Prepared analogously using [(Cp*RuCl)$_4$] (1.25 mol %) as the catalyst; colorless oil (74.3 mg, 83%) (α/β=94/6) (Z/E=98:2 for the major isomer (NMR)); $^1$H NMR (400 MHz, CDCl$_3$): δ=6.07 (td, J=7.1, 1.1, J$_{Sn-H}$=138.1 Hz, 1H), 3.67-3.54 (m, 1H), 2.38-2.19 (m, 1H), 2.02 (qd, J=7.2, 2.5 Hz, 2H), 1.55-1.40 (m, 7H), 1.39-1.24 (m, 10H), 1.15 (d, J=6.3 Hz, 3H), 1.03 (d, J=6.8 Hz, 3H), 0.98-0.81 (m, 9H), 0.89 (t, J=7.2 Hz, 9H); $^{13}$C NMR (101 MHz, CDCl$_3$): δ=147.0, 141.1, 69.7, 49.6, 35.1, 32.7, 29.4, 27.6, 22.8, 21.2, 14.4, 14.3, 13.8, 11.0; $^{119}$Sn NMR (112 MHz, CDCl$_3$) δ=−52.2; IR (v$_{max}$/cm$^{-1}$): 3350, 2956, 2923, 2871, 2854, 1458, 1376, 1249, 1075, 1019; ESI-MS calcd for C$_{22}$H$_{45}$OSn (M−H$^+$) 445.24972. found 445.25022.

EXAMPLE 26

2-((Z)-1-(Tributylstannyl)hex-1-en-1-yl)cyclopentan-1-ol

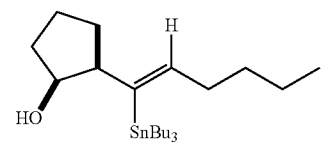

Prepared analogously using [(Cp*RuCl)$_4$] (1.25 mol %) as the catalyst; colorless oil (80.5 mg, 88%) (α/β=96/4) (Z/E=99:1 for the major isomer (NMR)); $^1$H NMR (400 MHz, CDCl$_3$): δ=6.08 (td, J=7.1, 1.1, J$_{Sn-H}$=133.4 Hz, 1H), 3.85 (q, J=7.1 Hz, 1H), 2.51-2.26 (m, 1H), 2.09-1.93 (m, 3H), 1.86 (dtd, J=12.5, 8.3, 4.0 Hz, 1H), 1.79-1.67 (m, 1H), 1.58 (dddd, J=16.9, 12.3, 6.3, 3.3 Hz, 3H), 1.52-1.41 (m, 6H), 1.40-1.23 (m, 11H), 1.01-0.79 (m, 9H), 0.89 (t, J=7.3 Hz, 9H); $^{13}$C NMR (101 MHz, CDCl$_3$): δ=145.0, 141.5, 77.7, 34.7, 33.2, 32.7, 31.0, 29.4, 27.6, 22.8, 21.0, 14.2, 13.8,

EXAMPLE 27

(Z)-3-Methyl-4-(tributylstannyl)hex-4-en-1-ol

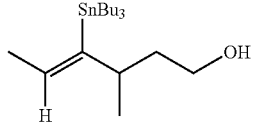

Prepared analogously using [(Cp*RuCl$_2$)$_n$] (5 mol %) as the catalyst and 1.15 equiv HSnBu$_3$; colorless oil (66.6 mg, 83%) (α/β=96/4) (Z/E=99:1 for the major isomer (NMR)); $^1$H NMR (400 MHz, CDCl$_3$): δ=6.13 (qd, J=6.6, 0.9, $_{Sn-H}$=134.1 Hz, 1H), 3.60 (tdd, J=6.6, 5.4, 1.5 Hz, 2H), 2.54-2.26 (m, 1H), 1.70 (d, J=6.5 Hz, 3H), 1.63-1.38 (m, 8H), 1.39-1.26 (m, 7H), 1.03-0.84 (m, 6H), 0.98 (d, J=6.9 Hz, 3H), 0.89 (t, J=7.3 Hz, 9H); $^{13}$C NMR (101 MHz, CDCl$_3$): δ=151.2, 133.1, 62.0, 41.8, 39.9, 29.4, 27.6, 22.1, 19.7, 13.8, 11.1; $^{119}$Sn NMR (112 MHz, CDCl$_3$) δ=−55.1; IR (ν$_{max}$/cm$^{-1}$): 3314, 2955, 2923, 2871, 2853, 1456, 1376, 1290, 1150, 1068, 1051, 1011; ESI-MS calcd for C$_{19}$H$_{39}$OSn (M−H$^+$) 403.20277. found 403.20295.

EXAMPLE 28

(Z)-7-Hydroxy-8-(tributylstannyl)oxacyclododec-8-en-2-one

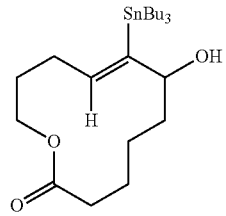

Prepared analogously using [(Cp*RuCl$_2$)$_n$] (5 mol %) as the catalyst and 1.15 equiv HSnBu$_3$; colorless oil (44.8 mg, 86%) (α/β=95/5) (Z/E=96:4 for the major isomer (NMR)); $^1$H NMR (400 MHz, CDCl$_3$): δ=6.29 (ddd, J=10.3, 3.6, 0.9 Hz, 1H), 4.54-4.27 (m, 1H), 4.26-3.98 (m, 2H), 2.51-2.38 (m, 2H), 2.21-2.05 (m, 2H), 1.99-1.87 (m, 1H), 1.87-1.76 (m, 2H), 1.70 (tdd, J=12.7, 5.0, 2.7 Hz, 1H), 1.56-1.39 (m, 8H), 1.37-1.26 (m, 8H), 1.15-1.03 (m, 1H), 1.02-0.86 (m, 6H), 0.89 (t, J=7.3 Hz, 9H); $^{13}$C NMR (101 MHz, CDCl$_3$): δ=173.2, 144.9, 143.3, 80.1, 66.0, 35.5, 34.4, 33.3, 29.4, 28.3, 27.6, 24.8, 22.1, 13.8, 11.3; $^{119}$Sn NMR (112 MHz, CDCl$_3$) δ=−59.8; IR (ν$_{max}$/cm$^{-1}$): 3486, 2953, 2921, 2870, 2852, 1733, 1455, 1376, 1293, 1248, 1156, 1072, 1016; ESI-MS calcd for C$_{23}$H$_{44}$O$_3$SnNa (M+Na$^+$) 511.22039. found 511.22072.

EXAMPLE 29

Ethyl (Z)-4-hydroxy-3-(tributylstannyl)hept-2-enoate

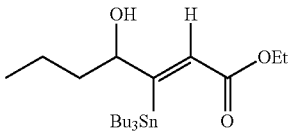

Prepared analogously using [(Cp*RuCl)$_4$] (1.25 mol %) as the catalyst; the HSnBu$_3$ was added dropwise over 20 min; pale yellow oil (61.0 mg, 66%) (α/β=97/3) (Z/E=99:1 for the major isomer (NMR)); $^1$H NMR (400 MHz, CDCl$_3$): δ=6.61 (d, J=1.5, J$_{Sn-H}$=102.0 Hz, 1H), 4.44 (dtd, J=7.7, 4.1, 1.7 Hz, 1H), 4.18 (qd, J=7.1, 2.9 Hz, 2H), 1.60 (d, J=4.0 Hz, 1H), 1.58-1.35 (m, 10H), 1.35-1.23 (m, 9H), 1.10-0.80 (m, 9H), 0.88 (t, J=7.3 Hz, 9H); $^{13}$C NMR (101 MHz, CDCl$_3$): δ=176.7, 168.1, 126.0, 77.0, 60.5, 39.0, 29.4, 27.6, 19.2, 14.5, 14.1, 13.8, 11.8; $^{119}$Sn NMR (112 MHz, CDCl$_3$) δ=−52.2; IR (ν$_{max}$/cm$^{-1}$): 3382, 2956, 2921, 2871, 2853, 1702, 1463, 1368, 1304, 1188, 1132, 1044; ESI-MS calcd for C$_{21}$H$_{42}$O$_3$SnNa (M+Na$^+$) 485.20474. found 485.20519.

EXAMPLE 30

(Z)-4-Phenyl-3-(tributylstannyl)but-3-en-2-ol

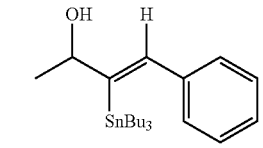

Prepared analogously using [(Cp*RuCl)$_4$] (1.25 mol %) as the catalyst; colorless oil (73.1 mg, 84%) (α/β=99/1) (Z/E=99:1 for the major isomer (NMR)); $^1$H NMR (400 MHz, CDCl$_3$): δ=7.46 (s, J$_{Sn-H}$=122.6 Hz, 1H), 7.36-7.24 (m, 3H), 7.24-7.18 (m, 2H), 4.69-4.50 (m, 1H), 1.63 (d, J=4.1 Hz, 1H), 1.49-1.32 (m, 9H), 1.31-1.19 (m, 6H), 0.87 (t, J=7.2 Hz, 9H), 0.84-0.68 (m, 6H); $^{13}$C NMR (101 MHz, CDCl$_3$): δ=154.3, 140.8, 138.5, 128.2, 128.0, 127.1, 75.1, 29.2, 27.5, 24.4, 13.8, 11.6; $^{119}$Sn NMR (112 MHz, CDCl$_3$) δ=−51.1; IR (ν$_{max}$/cm$^{-1}$): 3350, 2955, 2921, 2870, 2852, 1491, 1457, 1419, 1376, 1289, 1124, 1071; ESI-MS calcd for C$_{22}$H$_{37}$OSn (M−H$^+$) 437.18712. found 437.18732.

EXAMPLE 31

(2Z,4E)-2-(Tributylstannyl)nona-2,4-dien-1-ol

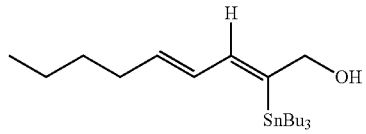

Prepared analogously using [(Cp*RuCl)$_4$] (1.25 mol %) as the catalyst; the HSnBu$_3$ was added as a solution in 0.5 mL CH$_2$Cl$_2$ over 2 h and the product was purified by column chromatography (Al$_2$O$_3$), pale yellow oil (54.4 mg, 60%) (α/β=99/1) (Z/E=87:13 for the major isomer (NMR)) isolated as pure Z-isomer. $^1$H NMR (400 MHz, CDCl$_3$): δ=6.78 (dq, J=10.4, 1.2, J$_{Sn-H}$=116.6 Hz, 1H), 6.00 (ddt, J=15.0, 10.5, 1.5 Hz, 1H), 5.73 (dt, J=14.5, 6.9 Hz, 1H), 4.34-4.18 (m, 2H), 2.15-2.07 (m, 2H), 1.60-1.41 (m, 6H), 1.41-1.20 (m, 11H), 1.09-0.91 (m, 6H), 0.90 (t, J=7.1 Hz, 3H), 0.89 (t, J=7.3 Hz, 9H); $^{13}$C NMR (101 MHz, CDCl$_3$): δ=146.2, 140.3, 136.9, 131.1, 70.5, 32.5, 31.3, 29.3, 27.5, 22.3, 14.1, 13.8, 10.5; $^{119}$Sn NMR (112 MHz, CDCl$_3$) δ=−50.2; IR (ν$_{max}$/cm$^{-1}$): 3323, 2955, 2922, 2871, 2853, 1463, 1376, 1291, 1071, 1001, 958; ESI-MS calcd for C$_{21}$H$_{41}$OSn (M−H$^+$) 429.21842. found 429.21862.

EXAMPLE 32

(2E,4E)-Hexa-2,4-dien-1-yl(Z)-6-hydroxy-7-(tributylstannyl) dodec-7-enoate

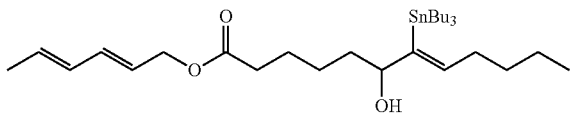

Prepared analogously using [(Cp*RuCl)$_4$] (1.25 mol %) as the catalyst; HSnBu$_3$ was added as a solution in 0.5 mL CH$_2$Cl$_2$ over 2 h; pale yellow oil (43.5 mg, 37%) (α/β=96/4) (Z/E=99:1 for the major isomer (NMR)). $^1$H NMR (400 MHz, CDCl$_3$): δ=6.24 (dd, J=15.2, 10.4 Hz, 1H), 6.13 (td, J=7.2, 1.0, J$_{Sn-H}$=128.7 Hz, 1H), 6.05 (ddd, J=15.0, 10.4, 1.7 Hz, 1H), 5.81-5.68 (m, 1H), 5.61 (dt, J=14.5, 6.6 Hz, 1H), 4.56 (d, J=6.6 Hz, 2H), 4.19-3.98 (m, 1H), 2.38-2.26 (m, 2H), 2.08-1.95 (m, 2H), 1.79-1.73 (m, 3H), 1.68-1.59 (m, 2H), 1.56-1.41 (m, 6H), 1.42-1.22 (m, 15H), 1.04-0.80 (m, 9H), 0.89 (t, J=7.2 Hz, 9H); $^{13}$C NMR (101 MHz, CDCl$_3$): δ=173.6, 147.7, 141.2, 134.9, 131.4, 130.6, 123.9, 80.2, 63.0, 37.4, 34.5, 34.1, 32.4, 29.4, 27.6, 25.7, 25.0, 22.7, 18.3, 14.2, 13.9, 11.2; $^{119}$Sn NMR (112 MHz, CDCl$_3$) δ=−55.2; IR (ν$_{max}$/cm$^{-1}$): 3502, 2954, 2923, 2871, 2854, 1736, 1458, 1377, 1230, 1157, 1071, 987; ESI-MS calcd for C$_{30}$H$_{55}$O$_3$SnNa (M+Na$^+$) 607.31429. found 607.31469.

EXAMPLE 33

(Z)-2-(1-(Tributylstannyl)dec-1-en-1-yl)-1H-indole

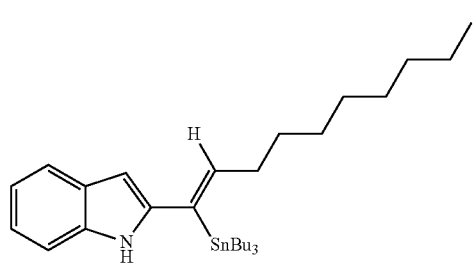

Prepared analogously using [(Cp*RuCl)$_4$] (1.25 mol %); the compound was purified by column chromatography over Al$_2$O$_3$; orange oil (88.3 mg, 81%) (α/β=95/5) (Z/E=99:1 for the major isomer (NMR)); $^1$H NMR (400 MHz, CDCl$_3$): δ=7.98-7.88 (bs, 1H), 7.53 (d, J=7.7 Hz, 1H), 7.29 (dq, J=8.0, 1.0 Hz, 1H), 7.11 (ddd, J=8.1, 7.1, 1.3 Hz, 1H), 7.05 (ddd, J=8.2, 7.1, 1.2 Hz, 1H), 6.57 (t, J=7.3, J$_{Sn-H}$=117.4 Hz, 1H), 6.20 (dd, J=2.2, 0.9 Hz, 1H), 2.21 (q, J=7.4 Hz, 2H), 1.62-1.41 (m, 8H), 1.41-1.23 (m, 16H), 1.15-0.95 (m, 6H), 0.94-0.85 (m, 12H); $^{13}$C NMR (101 MHz, CDCl$_3$): δ=144.1, 143.4, 136.0, 134.3, 129.4, 121.5, 120.1, 119.7, 110.4, 100.7, 35.2, 32.0, 30.3, 29.8, 29.7, 29.5, 29.2, 27.5, 22.8, 14.3, 13.8, 11.6; $^{119}$Sn NMR (112 MHz, CDCl$_3$) δ=−47.8; IR (ν$_{max}$/cm$^{-1}$): 3417, 2955, 2922, 2870, 2852, 1454, 1376, 1342, 1290, 1072, 1014; ESI-MS calcd for C$_{30}$H$_{50}$NSn (M−H$^+$) 544.29700. found 544.29749.

EXAMPLE 34

(Z)-N-(3-(Tributylstannyl)pent-3-en-1-yl)acetamide

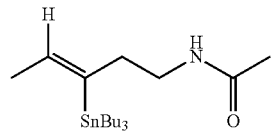

Prepared analogously using [(Cp*RuCl$_2$)$_n$] (5 mol %) as the catalyst and 1.15 equiv HSnBu$_3$; colorless oil (81.8 mg, 98%) (α/β=87/13) (Z/E=94:6 for the major isomer (NMR)); $^1$H NMR (400 MHz, CDCl$_3$): δ=6.16 (dt, J=6.5, 1.3, J$_{Sn-H}$=126.9 Hz, 1H), 5.42-5.28 (bs, 1H), 3.21 (td, J=6.8, 5.4 Hz, 2H), 2.44-2.25 (m, 2H), 1.95 (s, 3H), 1.73 (dt, J=6.5, 1.0 Hz, 3H), 1.56-1.39 (m, 6H), 1.37-1.24 (m, 6H), 1.02-0.84 (m, 6H), 0.89 (t, J=7.3 Hz, 9H); $^{13}$C NMR (101 MHz, CDCl$_3$): δ=169.9, 141.7, 137.4, 40.1, 39.2, 29.4, 27.5, 23.5, 20.1, 13.8, 10.2; $^{119}$Sn NMR (112 MHz, CDCl$_3$) δ=−52.5; IR (ν$_{max}$/cm$^{-1}$): 3281, 3084, 2955, 2922, 2871, 2852, 1649, 1556, 1456, 1375, 1293, 1206, 1071; ESI-MS calcd for C$_{19}$H$_{39}$NOSnNa (M+Na$^+$) 440.19451. found 440.19479.

EXAMPLE 35

(Z)-1,1,1-Trifluoro-N-(3-(tributylstannyl)pent-3-en-1-yl)methane-sulfonamide

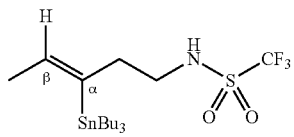

Prepared analogously with (Cp*RuCl$_2$)$_n$ in CH$_2$Cl$_2$, pale yellow oil (79 mg, 78%, α only, Z/E=91:1 (NMR)). $^1$H NMR (400 MHz, CDCl$_3$): δ=6.21 (qt, J=6.6, 1.2 Hz, 1H), 4.77 (s (br), NH), 3.25 (q, J=5.6, 2H), 2.46 (t, J=6.6, 2H) 1.75 (d, J=6.4, 3H), 1.52-1.43 (m, 6H), 1.37-1.27 (m, 6H), 0.97-0.92 (m, 6H), 0.90 (t, J=7.2, 9H); $^{13}$C NMR (101 MHz, CDCl$_3$): δ=139.7, 139.6, 119.7 (q, J=320 Hz), 43.6, 40.6, 29.2, 27.3, 20.0, 13.6, 10.0; $^{119}$Sn (112 MHz, CDCl$_3$): δ=−51.4; IR (film/cm$^{-1}$) ṽ=3308, 2957, 2924, 2873, 2853, 1620, 1420, 1373, 1230, 1187, 1147, 1065, 962, 875, 864, 845; ESI-MS calcd for C$_{18}$H$_{35}$F$_3$NO$_2$SSn (M−H) 506.13674. found 506.13716.

EXAMPLE 36

(Z)-2,2,2-Trifluoro-N-(3-(tributylstannyl)pent-3-en-1-yl)acetamide

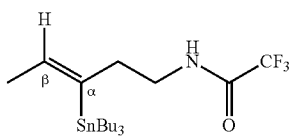

Prepared analogously with (Cp*RuCl$_2$)$_n$ in CH$_2$Cl$_2$; colorless oil (87 mg, 90%, α:β=95:5, Z/E=95:5 for the major isomer (NMR)). $^1$H NMR (400 MHz, CDCl$_3$): δ=6.20 (q, J=6.5 Hz, 1H+NH), 3.32 (q, J=6.2, 2H), 2.43 (t, J=6.6, 2H) 1.75 (d, J=6.5 Hz, 3H), 1.51-1.42 (m, 6H), 1.36-1.27 (m, 6H), 0.98-0.92 (m, 6H), 0.90 (t, J=7, 9H); $^{13}$C NMR (101 MHz, CDCl$_3$): δ=156.8 (q, J=36 Hz), 140.4, 138.6, 115.9 (q, J=288 Hz), 39.3, 39.1, 29.2, 27.3, 19.9, 13.6, 10.0; $^{119}$Sn (112 MHz, CDCl$_3$): δ=−51.4; IR (film/cm$^{-1}$) $\tilde{v}$=3303, 3102, 2957, 2924, 2873, 2853, 1701, 1620, 1558, 1457, 1376, 1340, 1293, 1204, 1161, 1072, 1022, 960, 875, 864, 831, 769, 724, 688, 665; ESI-MS calcd for C$_{19}$H$_{36}$F$_3$NOSnNa (M+Na$^+$) 494.16625. found 494.16661.

EXAMPLE 37 tert-Butyl (Z)-(3-(tributylstannyl)pent-3-en-1-yl)carbamate

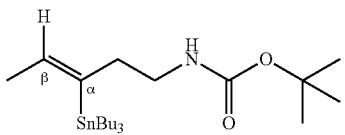

Prepared analogously with (Cp*RuCl$_2$)$_n$ in CH$_2$Cl$_2$; pale yellow oil (88 mg, 92%, α:β=77:23; Z/E=96:1 for the major isomer (NMR)). $^1$H NMR (400 MHz, CDCl$_3$): δ=6.15 (q, J=6.5 Hz), 4.43 (s (br), NH), 3.08 (m), 2.32 (t, J=6.5 Hz), 1.72 (d, J=6.5 Hz), 1.53-1.42 (m), 1.44 (s), 1.36-1.26 (m), 0.95-0.85 (m); $^{13}$C NMR (101 MHz, CDCl$_3$): δ=155.8, 141.3, 137.2, 78.9, 40.4, 35.1, 29.2, 28.4, 27.4, 20.0, 13.7, 10.0; $^{119}$Sn (112 MHz, CDCl$_3$): δ=−52.2; IR (film/cm$^{-1}$) $\tilde{v}$=3443, 3366, 2956, 2924, 2872, 2853, 1706, 1620, 1502, 1456, 1390, 1376, 1365, 1340, 1248, 1071, 1021, 998, 961, 872, 834, 778, 688, 666; ESI-MS calcd for C$_{22}$H$_{45}$NOSnNa (M+Na$^+$) 498.23638. found 498.23692.

EXAMPLE 38

(Z)-3-(Tributylstannyl)hexadec-2-en-14-yn-4-ol

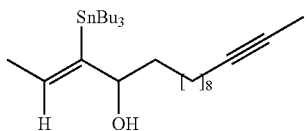

Prepared analogously using [(Cp*RuCl)$_4$] (1.25 mol %) as the catalyst and 1.05 equiv. of Bu$_3$SnH; purification by flash chromatography (hexane/EtOAc, 100/1→20/1) allowed minor by-products to be removed and gave the title compound as a colorless oil (57.7 mg, 55%). $^1$H NMR (400 MHz, CDCl$_3$): δ=6.23 (qd, J=6.6, 1.0, J$_{Sn-H}$=126.0 Hz, 1H), 4.20-3.98 (m, 1H), 2.11 (tq, J=7.3, 2.5 Hz, 2H), 1.78 (t, J=2.5 Hz, 3H), 1.73 (d, J=6.5 Hz, 3H), 1.57-1.40 (m, 9H), 1.40-1.18 (m, 20H), 1.06-0.87 (m, 6H), 0.89 (t, J=7.3 Hz, 9H); $^{13}$C NMR (101 MHz, CDCl$_3$): δ=149.6, 134.8, 80.5, 79.6, 75.4, 37.9, 29.8, 29.7, 29.4, 29.34, 29.27, 29.1, 27.6, 26.1, 19.4, 18.9, 13.8, 11.1, 3.6; $^{119}$Sn NMR (112 MHz, CDCl$_3$): δ=−55.2 ppm; IR (film, cm$^{-1}$): $\tilde{v}$=3468, 2954, 2922, 2853, 1462, 1375, 1290, 1148, 1070, 1046, 1004; ESI-MS calcd for C$_{28}$H$_{54}$OSnNa (M+Na$^+$) 549.30881. found 549.30917.

EXAMPLE 39

4-(Trimethylsilyl)but-3-yn-1-yl 4-(tributylstannyl)pent-4-enoate

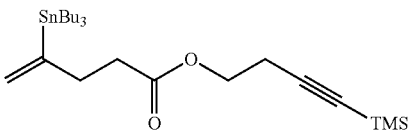

Prepared according to the procedure detailed in Example 1 using [Cp*Ru(MeCN)$_3$]PF$_6$ as the catalyst and exactly 1.0 equiv. of Bu$_3$SnH; colorless oil (isomer ratio for stannylation at the terminal versus the silylated triple bond=93:7) (98.2 mg, 96%); data of major isomer: $^1$H NMR (400 MHz, CDCl$_3$): δ=5.70 (dt, J=2.3, 1.6, J$_{Sn-H}$=133.2 Hz, 1H), 5.15 (dt, J=2.3, 1.2, J$_{Sn-H}$=62.4 Hz, 1H), 4.16 (t, J=7.1 Hz, 2H), 2.64-2.46 (m, 4H), 2.46-2.34 (m, 2H), 1.59-1.40 (m, 6H), 1.38-1.25 (m, 6H), 1.00-0.82 (m, 15H), 0.15 (s, 9H); $^{13}$C NMR (101 MHz, CDCl$_3$): δ=173.0, 153.1, 125.6, 102.4, 86.6, 62.3, 35.8, 34.1, 29.2, 27.5, 20.5, 13.8, 9.7, 0.2; $^{119}$Sn NMR (112 MHz, CDCl$_3$): δ=−44.0 ppm; IR (film, cm$^{-1}$): $\tilde{v}$=2956, 2925, 2872, 2853, 2181, 1741, 1457, 1419, 1377, 1337, 1248, 1162, 1071, 1026; ESI-MS calcd for C$_{24}$H$_{46}$O$_2$SiSnNa (M+Na$^+$) 537.21806. found 537.21852.

EXAMPLE 40

Pent-3-yn-1-yl 4-(tributylstannyl)pent-4-enoate

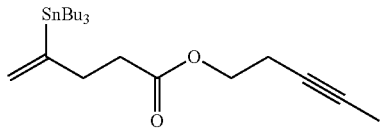

Prepared according to the procedure detailed in Example 1 using [Cp*Ru(MeCN)$_3$]PF$_6$ as the catalyst and exactly 1.0 equiv. of Bu$_3$SnH; colorless oil (isomer ratio for stannylation at the terminal versus the internal triple bond=76:24) (80.6 mg, 89%); $^1$H NMR (400 MHz, CDCl$_3$): δ=5.70 (dq, J=3.5, 1.7, J$_{Sn-H}$=135.0 Hz, 1H), 5.15 (dq, J=2.0, 1.0, J$_{Sn-H}$=62.6 Hz, 1H), 4.13 (t, J=7.0 Hz, 2H), 2.65-2.50 (m, 2H), 2.50-2.34 (m, 4H), 1.77 (t, J=2.5 Hz, 3H), 1.63-1.38 (m, 6H), 1.37-1.23 (m, 6H), 1.01-0.82 (m, 6H), 0.89 (t, J=7.3 Hz, 9H); $^{13}$C NMR (101 MHz, CDCl$_3$): δ=173.1, 153.2, 125.5, 77.4, 74.9, 62.9, 35.8, 34.0, 29.2, 27.5, 19.4, 13.8, 9.7, 3.6; $^{119}$Sn NMR (112 MHz, CDCl$_3$): δ=−44.0 ppm; IR (film, cm$^{-1}$): ṽ=2955, 2922, 2871, 2852, 1739, 1457, 1419, 1377, 1340, 1245, 1165, 1072, 1002; ESI-MS calcd for C$_{22}$H$_{40}$O$_2$SnNa (M+Na$^+$) 479.19418. found 479.19459.

EXAMPLE 41

(Z)-Tributyl(1-(4-(trifluoromethyl)phenyl)prop-1-en-1-yl)stannane

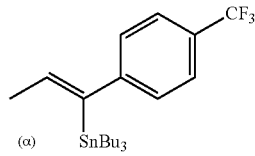

Prepared according to the procedure detailed in Example 1 using [Cp*Ru(MeCN)$_3$]PF$_6$ as the catalyst; colorless oil (88.4 mg, 93%) (α/β=65:35) (Z/E=99:1, α-isomer (NMR)); Data of major α-isomer: $^1$H NMR (500 MHz, CD$_2$Cl$_2$): δ=7.53-7.48 (m, 2H), 7.12 (d, J=7.9 Hz, 2H), 6.32 (q, J=6.7 Hz, 1H), 1.91 (d, J=6.7 Hz, 3H), 1.51-1.40 (m, 6H), 1.32-1.24 (m, 6H), 1.05-0.89 (m, 6H), 0.86 (t, J=7.3 Hz, 9H); $^{13}$C NMR (126 MHz, CD$_2$Cl$_2$, resolved signals): δ=152.7, 146.2, 140.3, 127.7, 127.3, 125.4, 125.4, 125.4, 125.3, 29.6, 27.9, 20.8, 14.0, 11.4; $^{119}$Sn NMR (186 MHz, CD$_2$Cl$_2$): δ=−48.1 ppm; IR (film, cm$^{-1}$): ṽ=2957,

EXAMPLE 42

(Z)-Trimethyl(2-(tributylstannyl)oct-2-en-1-yl)silane

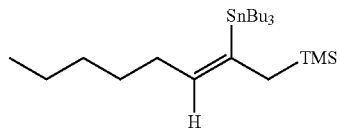

Prepared according to the procedure detailed in Example 1 using [Cp*Ru(MeCN)$_3$]PF$_6$ (5 mol %) as the catalyst; colorless oil (38.7 mg, 82%) (α/β=79/21) (Z/E=95:5 for the major isomer (NMR)). $^1$H NMR (400 MHz, CDCl$_3$): δ=5.84 (tt, J=7.2, 1.2, J$_{Sn-H}$=139.7 Hz, 1H), 1.95 (q, J=7.0 Hz, 2H), 1.66 (s, 2H), 1.58-1.40 (m, 6H), 1.38-1.22 (m, 12H), 0.98-0.80 (m, 18H), −0.03 (s, 9H); $^{13}$C NMR (101 MHz, CDCl$_3$): δ=139.1, 138.6, 35.8, 31.9, 30.6, 29.4, 29.0, 27.7, 22.9, 14.3, 13.8, 10.7, −1.2; $^{119}$Sn NMR (112 MHz, CDCl$_3$) δ=−53.6; IR (v$_{max}$/cm$^{-1}$): 2955, 2923, 2871, 2854, 1463, 1377, 1246, 1149, 1071, 837; EI-MS calcd for C$_{23}$H$_{50}$SiSn (M+Na$^+$) 474.27031. found 474.27003.

The invention claimed is:
1. A process for highly stereoselective trans-hydrostannation of alkynes comprising the steps of reacting an alkyne of the formula (I)

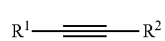
(I)

with a tin hydride of the formula X$^1$X$^2$X$^3$SnH in the presence of a ruthenium catalyst to yield an alkene of the formula (II):

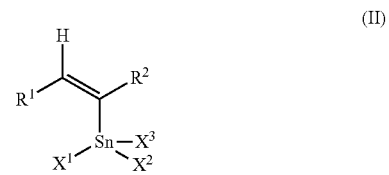
(II)

Wherein:
R$^1$ and R$^2$ are the same or different and are each selected from:
I. straight chain or branched chain aliphatic hydrocarbons, or cyclic aliphatic hydrocarbons, said aliphatic hydrocarbons optionally having heteroatoms and/or aromatic hydrocarbons and/or heteroaromatic hydrocarbons in the chain and/or having one or more substituents selected from C$_1$-C$_{20}$-alkyl, C$_5$-C$_8$-heterocycloalkyl or C$_6$ to C$_{20}$ aromatic hydrocarbon, C$_5$ to C$_{20}$ heteroaromatic hydrocarbon or aryl-(C$_1$-C$_6$)-alkyl, heteroaryl-(C$_1$-C$_6$)-alkyl, or heteroatoms, or
II. aromatic hydrocarbons having 5 to 20 carbon atoms or heteroaromatic hydrocarbons having 1 to 20 carbon atoms, said aromatic or heteroaromatic hydrocarbons each optionally having one or more substituents selected from C$_1$-C$_{20}$-alkyl, C$_5$-C$_8$-heterocycloalkyl or C$_6$ to C$_{20}$ aromatic hydrocarbon, C$_5$ to C$_{20}$ heteroaromatic hydrocarbon or aryl-(C$_1$-C$_6$)-alkyl, heteroaryl-(C$_1$-C$_6$)-alkyl, heteroatoms, or
one of R$^1$ and R$^2$ is selected from hydrogen, halogen, or —SiR*RR*, wherein R*, R, R* can be the same or different and shave the meaning as given under I. and II., and the other of R$^1$ and R$^2$ has the meaning as given under I, and II, or
R$^1$ and R$^2$ together form an aliphatic hydrocarbon chain having 6 to 30 carbon atoms, optionally having heteroatoms and/or aromatic hydrocarbons in the chain and/or optionally having one or more substituents selected from C$_1$-C$_{20}$-alkyl, C$_5$-C$_8$-heterocycloalkyl or C$_6$ to C$_{20}$ aromatic hydrocarbon, C$_5$ to C$_{20}$ heteroaromatic hydrocarbon or aryl-(C$_1$-C$_6$)-alkyl, heteroaryl-(C$_1$-C$_6$)-alkyl, said aliphatic hydrocarbon chain optionally being substituted by one or more substituents selected from heterosubstituents, straight chain, branched chain, cyclic aliphatic C$_1$ to C$_{20}$ hydrocarbons, C$_6$ to C$_{20}$ aromatic hydrocarbon, C$_5$ to heteroaromatic hydrocarbon, aryl-(C$_1$-C$_6$)-alkyl, or heteroaryl-(C$_1$-C$_6$)-alkyl or heteroatoms;
wherein the substituents X$^1$, X$^2$ and X$^3$ in the formula X$^1$X$^2$X$^3$SnH are the same or different and are each selected from hydrogen, straight chain, branched chain or cyclic aliphatic hydrocarbons, aromatic hydrocarbons, or two of X$^1$ X$^2$ and X$^3$ together form an aliphatic hydrocarbon chain having 2 to 20 carbon atoms, said hydrocarbon group optionally having heteroatoms in the chain and/or optionally having one or more substituents selected from C$_1$-C$_{20}$-alkyl, C$_5$-C$_8$-heterocycloalkyl or C$_6$ to C$_{20}$ aromatic hydrocarbon, C$_1$ to C$_{20}$ heteroaromatic hydrocarbon or aryl-(C$_1$-C$_6$)-alkyl, heteroaryl-(C$_1$-C$_6$)-alkyl, having identical or different alkyl groups with 2 to 12 carbon atoms, halogen or heteroatoms wherein at least two of X$^1$, X$^2$ and X$^3$ are not hydrogen; and wherein the catalyst is a cyclopentadienyl-coordinated ruthenium complex containing the following substructure:

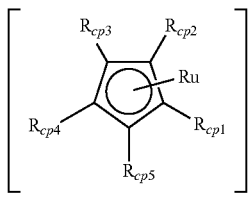

wherein $R_{cp1}$ to $R_{cp5}$ are the same or different and are each selected from hydrogen or from straight chain, branched chain or cyclic aliphatic hydrocarbons, optionally having heteroatoms and/or aromatic hydrocarbons in the chain and/or optionally having one or more substituents selected from $C_1$-$C_{20}$-alkyl, heterocycloalkyl, $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl or heteroatoms and wherein further ligands are coordinated to the central atom Ruthenium.

2. Process for highly stereoselective trans-hydrostannation of alkynes according to claim 1 wherein $R^1$ and $R^2$ are the same or different and are each selected from straight chain or branched chain aliphatic hydrocarbons having 1 to 20 carbon atoms optionally having heteroatoms and/or aromatic hydrocarbons in the chain or aromatic hydrocarbons having 5 to 20 carbon atoms, optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, or heteroatoms, or $R^1$ and $R^2$ together form an aliphatic hydrocarbon chain structure having 8 to 20 carbon atoms, optionally having heteroatoms and/or aromatic hydrocarbons in the chain and/or optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, said chain structure optionally being substituted by one or more substituents selected from heterosubstituents, straight chain, branched chain, cyclic aliphatic $C_1$ to $C_{20}$ hydrocarbons, $C_6$ to $C_{20}$ aromatic hydrocarbon, $C_5$ to $C_{20}$ heteroaromatic hydrocarbon, aryl-($C_1$-$C_6$)-alkyl, or heteroaryl-($C_1$-$C_6$)-alkyl, or one of $R^1$ and $R^2$ is selected from hydrogen, halogen, —SiR*RR*, wherein R*, R, R* are the same or different and are each selected from straight chain or branched chain aliphatic hydrocarbons having 1 to 20 carbon atoms optionally having heteroatoms and/or aromatic hydrocarbons in the chain or aromatic hydrocarbons having 5 to 20 carbon atoms, optionally having one or more substituents selected from $C_1$-$C_{20}$-alkyl, $C_5$-$C_8$-heterocycloalkyl or $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl, or heteroatoms.

3. Process for highly stereoselective trans-hydrostannation of alkynes according to claim 1 wherein the substituents $X^1$, $X^2$ and $X^3$ in the formula $X^1X^2X^3$ SnH are the same or different and are each selected from straight chain, branched chain or cyclic $C_1$ to $C_{10}$ aliphatic hydrocarbons each optionally being substituted by methyl, ethyl, propyl, butyl or isomers thereof, or one or more fluorine atoms.

4. Process for highly stereoselective trans-hydrostannation of alkynes according to claim 1 wherein the catalyst used in the inventive process is a cyclopentadienyl-coordinated ruthenium complex comprising the following substructure:

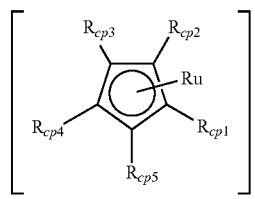

wherein $R_{cp1}$ to $R_{cp5}$ are the same or different and are each selected from hydrogen or from straight chain, branched chain or cyclic aliphatic hydrocarbons, optionally having heteroatoms and/or aromatic hydrocarbons in the chain and/or optionally having one or more substituents selected from $C_1$-$C_{20}$-alkyl, heterocycloalkyl, $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl or heteroatoms and wherein further ligands coordinated to the central atom ruthenium.

5. Process for highly stereoselective trans-hydrostannation of alkynes according claim 1 wherein the catalyst is $[Cp*RuL_3]X$ wherein $Cp*=\eta^5$-$C_5R_{5cp}$ with each $R_{cp}$ being H or $CH_3$, and L being the same or different ligand/substituent and being selected from electron-donating ligands/substituents, or wherein the catalyst is a complex of the formula $[Cp*RuY_n]$ wherein $Cp*=\eta^5$-$C_5R_{5cp}$ with each $R_{cp}$ being H or $CH_3$, and Y is an anionic ligand being selected from hydrogen, halogen and n=2, 3, or a dimer or oligomer of the formula $[Cp*RuY_2]_n$ wherein $Cp*=\eta^5$-$C_5R_5$ with R being H or $CH_3$ and Y is an anionic ligand and being selected from hydrogen, halogen and n≥2.

6. Process for highly stereoselective trans-hydroboration of internal alkynes according to claim 1 wherein the following complex is used as catalyst:

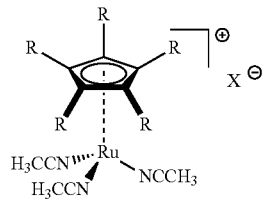

wherein the substituent R is selected from H or Me and $X^\ominus$ is an anionic counter ion.

7. Process for highly stereoselective trans-hydrostannation of alkynes according to claim 5 wherein the anionic counterion is selected from $PF_6^-$, $SbF_6^-$, $BF_4^-$, $ClO_4^-$, $F_3CCOO^-$, $Tf_2N^-$, (Tf=trifluoromethanesulfonyl), $TfO^-$, tosyl, $[B[3,5-(CF_3)_2C_6H_3]_4]^-$, $B(C_6F_5)_4^-$ or $Al(OC(CF_3)_3)_4^-$.

8. Process for highly stereoselective trans-hydrostannation of alkynes according to claim 1 wherein the catalyst is selected from the following complexes:

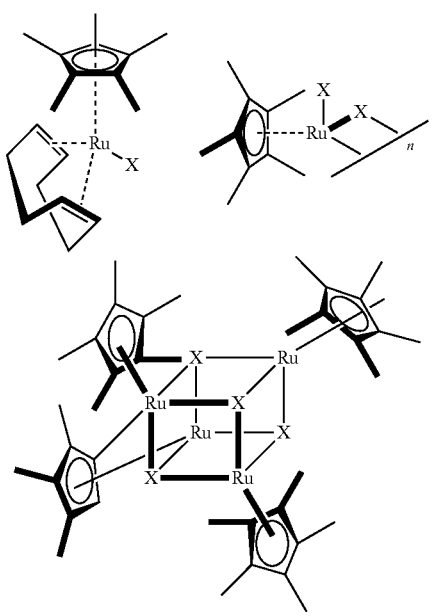

wherein the substituent X is selected from Cl, Br, I, and n is ≥2.

9. Process for highly stereoselective trans-hydrostannation of unsymmetrical alkynes according to claim 1, in which the catalyst is selected depending on the alkyne in order to control the ratio of regioisomers formed.

10. A process comprising conducting a hydrostannation reaction in the presence of an organic tin compound and a catalyst, wherein the catalyst is a ruthenium catalyst comprising a cyclopentadienyl-coordinated ruthenium complex comprising the following substructure:

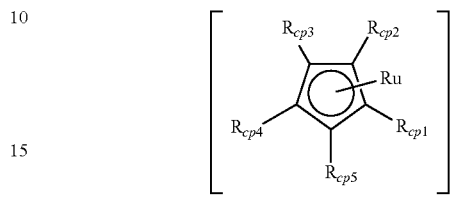

wherein $R_{cp1}$ to $R_{cp5}$ are the same or different and are each selected from hydrogen or from straight chain, branched chain or cyclic aliphatic hydrocarbons, optionally having heteroatoms and/or aromatic hydrocarbons in the chain and/or optionally having one or more substituents selected from $C_1$-$C_{20}$-alkyl, heterocycloalkyl, $C_6$ to $C_{20}$ aromatic hydrocarbon, $C_5$ to $C_{20}$ heteroaromatic hydrocarbon or aryl-($C_1$-$C_6$)-alkyl, heteroaryl-($C_1$-$C_6$)-alkyl or heteroatoms and wherein further ligands L are coordinated to the central atom ruthenium.

* * * * *